United States Patent
Shabaz et al.

(10) Patent No.: US 11,246,574 B2
(45) Date of Patent: *Feb. 15, 2022

(54) BIOPSY DEVICE WITH APERTURE ORIENTATION AND IMPROVED TIP

(71) Applicant: SenoRx, Inc., Tempe, AZ (US)

(72) Inventors: Martin V. Shabaz, Lake Forest, CA (US); Richard L. Quick, Mission Viejo, CA (US); Frank R. Louw, Carlsbad, CA (US); Paul Lubock, Monarch Beach, CA (US); Jason H. Safabash, Alison Viejo, CA (US)

(73) Assignee: SenoRx, Inc., Franklin Lakes, NJ (US)

( * ) Notice: Subject to any disclaimer, the term of this patent is extended or adjusted under 35 U.S.C. 154(b) by 728 days.

This patent is subject to a terminal disclaimer.

(21) Appl. No.: 16/138,248

(22) Filed: Sep. 21, 2018

(65) Prior Publication Data

US 2019/0021705 A1     Jan. 24, 2019

Related U.S. Application Data

(60) Continuation of application No. 13/747,530, filed on Jan. 23, 2013, now Pat. No. 10,105,125, which is a
(Continued)

(51) Int. Cl.
*A61B 10/02*     (2006.01)
*A61B 17/32*     (2006.01)
(Continued)

(52) U.S. Cl.
CPC ...... *A61B 10/0233* (2013.01); *A61B 10/0275* (2013.01); *A61B 10/0283* (2013.01);
(Continued)

(58) Field of Classification Search
CPC ............ A61B 10/0233; A61B 10/0275; A61B 10/0283
See application file for complete search history.

(56) References Cited

U.S. PATENT DOCUMENTS

| 2,032,860 A | 3/1936 | Wappler et al. |
| 2,525,329 A | 10/1950 | Wyzenbeek |

(Continued)

FOREIGN PATENT DOCUMENTS

| DE | 1225813 B | 9/1966 |
| DE | 19528440 A1 | 2/1997 |

(Continued)

OTHER PUBLICATIONS

Written Opinion of the International Searching Authority for PCT/US99/21416 dated Jul. 18, 2000.
(Continued)

*Primary Examiner* — Daniel L Cerioni
*Assistant Examiner* — Yasmeen S Warsi
(74) *Attorney, Agent, or Firm* — Dinsmore & Shohl LLP

(57) ABSTRACT

A biopsy device includes an elongated probe having a central longitudinal axis, a proximal end, and a distal end. A tissue penetrating tip includes a proximal base and a sharp distal point. The proximal base is secured to the distal end of the elongated probe. The sharp distal point is distal to the proximal base and is aligned with the central longitudinal axis. The tissue penetrating tip has a plurality of concave surfaces annularly arranged to form at least three adjacent pairs of concave surfaces. Each concave surface of the plurality of concave surfaces extends from the proximal base to the sharp distal point. Each adjacent pair of concave surfaces intersect to form a concave curved cutting edge. Cumulatively, the at least three adjacent pairs of concave surfaces form a plurality of concave curved cutting edges that distally terminate at the sharp distal point.

14 Claims, 14 Drawing Sheets

Related U.S. Application Data continuation of application No. 11/981,024, filed on Oct. 31, 2007, now Pat. No. 8,360,990, which is a division of application No. 11/014,413, filed on Dec. 16, 2004, now Pat. No. 9,408,592.

(51) Int. Cl.
*A61B 17/3205* (2006.01)
*A61B 17/34* (2006.01)
*A61B 17/00* (2006.01)

(52) U.S. Cl.
CPC ... *A61B 17/32002* (2013.01); *A61B 17/32053* (2013.01); *A61B 17/3417* (2013.01); *A61B 2010/0208* (2013.01); *A61B 2010/0225* (2013.01); *A61B 2017/00473* (2013.01); *A61B 2017/3405* (2013.01)

(56) References Cited

U.S. PATENT DOCUMENTS

| | | |
|---|---|---|
| 3,341,417 A | 9/1967 | Sinaiko |
| 3,788,320 A | 1/1974 | Dye |
| 3,805,791 A | 4/1974 | Seuberth et al. |
| 3,818,894 A | 6/1974 | Wichterle et al. |
| 3,823,212 A | 7/1974 | Chvapil |
| 3,844,272 A | 10/1974 | Banko |
| 3,847,153 A | 11/1974 | Weissman |
| 3,910,279 A | 10/1975 | Okada et al. |
| 3,945,375 A | 3/1976 | Banko |
| 3,955,578 A | 5/1976 | Chamness et al. |
| 4,007,732 A | 2/1977 | Kvavle et al. |
| 4,172,449 A | 10/1979 | LeRoy et al. |
| 4,197,846 A | 4/1980 | Bucalo |
| 4,202,338 A | 5/1980 | Bitrolf |
| 4,234,048 A | 11/1980 | Rowley |
| 4,276,885 A | 7/1981 | Tickner et al. |
| 4,294,254 A | 10/1981 | Chamness |
| 4,311,143 A | 1/1982 | Komiya |
| 4,331,654 A | 5/1982 | Morris |
| 4,362,160 A | 12/1982 | Hiltebrandt |
| 4,503,855 A | 3/1985 | Maslanka |
| 4,545,367 A | 10/1985 | Tucci |
| 4,565,200 A | 1/1986 | Cosman |
| 4,576,162 A | 3/1986 | McCorkle |
| 4,638,802 A | 1/1987 | Okada |
| 4,643,187 A | 2/1987 | Okada |
| 4,647,480 A | 3/1987 | Ahmed |
| 4,666,438 A | 5/1987 | Raulerson |
| 4,682,606 A | 7/1987 | DeCaprio |
| 4,693,237 A | 9/1987 | Hoffman et al. |
| 4,718,419 A | 1/1988 | Okada |
| 4,724,836 A | 2/1988 | Okada |
| 4,813,062 A | 3/1989 | Gilpatrick |
| 4,847,049 A | 7/1989 | Yamamoto |
| 4,853,470 A | 8/1989 | Strupczewski |
| 4,909,250 A | 3/1990 | Smith |
| 4,926,858 A | 5/1990 | Gifford, III et al. |
| 5,007,908 A | 4/1991 | Rydell |
| 5,024,617 A | 6/1991 | Karpiel |
| 5,035,696 A | 7/1991 | Rydell |
| 5,041,124 A | 8/1991 | Kensey |
| 5,047,027 A | 9/1991 | Rydell |
| 5,057,082 A | 10/1991 | Burchette, Jr. |
| 5,059,204 A | 10/1991 | Lawson et al. |
| 5,064,424 A | 11/1991 | Bitrolf |
| 5,066,295 A | 11/1991 | Kozak et al. |
| 5,078,716 A | 1/1992 | Doll |
| 5,080,660 A | 1/1992 | Buelna |
| 5,085,659 A | 2/1992 | Rydell |
| RE33,925 E | 5/1992 | Bales et al. |
| 5,133,359 A | 7/1992 | Kedem |
| 5,133,360 A | 7/1992 | Spears |
| RE34,056 E | 9/1992 | Lindgren et al. |
| 5,147,307 A | 9/1992 | Gluck |
| 5,158,561 A | 10/1992 | Rydell et al. |
| 5,163,938 A | 11/1992 | Kambara et al. |
| 5,195,533 A | 3/1993 | Chin et al. |
| 5,196,007 A | 3/1993 | Ellman et al. |
| 5,197,846 A | 3/1993 | Uno et al. |
| 5,201,732 A | 4/1993 | Parins et al. |
| 5,201,741 A | 4/1993 | Dulebohn |
| 5,207,686 A | 5/1993 | Dolgin |
| 5,217,458 A | 6/1993 | Parins |
| 5,224,488 A | 7/1993 | Neuffer |
| 5,236,410 A | 8/1993 | Granov et al. |
| 5,281,218 A | 1/1994 | Imran |
| 5,281,408 A | 1/1994 | Unger |
| 5,282,781 A | 2/1994 | Liprie |
| 5,312,400 A | 5/1994 | Bales et al. |
| 5,318,564 A | 6/1994 | Eggers |
| 5,320,613 A | 6/1994 | Houge et al. |
| 5,323,768 A | 6/1994 | Saito et al. |
| 5,324,288 A | 6/1994 | Billings et al. |
| 5,334,381 A | 8/1994 | Unger |
| 5,335,671 A | 8/1994 | Clement |
| 5,344,420 A | 9/1994 | Hilal et al. |
| 5,368,030 A | 11/1994 | Zinreich et al. |
| 5,374,188 A | 12/1994 | Frank et al. |
| 5,376,094 A | 12/1994 | Kline |
| 5,380,321 A | 1/1995 | Yoon |
| 5,389,106 A | 2/1995 | Tower |
| 5,395,312 A | 3/1995 | Desai |
| 5,395,319 A | 3/1995 | Hirsch et al. |
| 5,415,656 A | 5/1995 | Tihon et al. |
| 5,417,687 A | 5/1995 | Nardella et al. |
| 5,417,697 A | 5/1995 | Wilk et al. |
| 5,422,730 A | 6/1995 | Barlow et al. |
| 5,423,809 A | 6/1995 | Klicek |
| 5,423,814 A | 6/1995 | Zhu et al. |
| 5,431,649 A | 7/1995 | Mulier et al. |
| 5,433,204 A | 7/1995 | Olson |
| 5,437,665 A | 8/1995 | Munro |
| 5,441,498 A | 8/1995 | Perkins |
| 5,441,503 A | 8/1995 | Considine et al. |
| 5,462,553 A | 10/1995 | Dolgin |
| 5,470,308 A | 11/1995 | Edwards et al. |
| 5,477,862 A | 12/1995 | Haaga |
| 5,484,436 A | 1/1996 | Eggers et al. |
| 5,487,385 A | 1/1996 | Avitall |
| 5,488,958 A | 2/1996 | Topel et al. |
| 5,494,030 A | 2/1996 | Swartz et al. |
| 5,501,654 A | 3/1996 | Failla et al. |
| 5,507,743 A | 4/1996 | Edwards et al. |
| 5,526,822 A | 6/1996 | Burbank et al. |
| 5,527,331 A | 6/1996 | Kresch et al. |
| 5,538,010 A | 7/1996 | Darr et al. |
| 5,542,948 A | 8/1996 | Weaver et al. |
| 5,549,560 A | 8/1996 | Van de Wijdeven |
| 5,578,030 A | 11/1996 | Levin |
| 5,595,185 A | 1/1997 | Erlich |
| 5,597,378 A | 1/1997 | Jervis |
| 5,599,347 A | 2/1997 | Hart et al. |
| 5,607,389 A | 3/1997 | Edwards et al. |
| 5,611,803 A | 3/1997 | Heaven et al. |
| 5,636,255 A | 6/1997 | Ellis |
| 5,643,246 A | 7/1997 | Leeb et al. |
| 5,643,282 A | 7/1997 | Kieturakis |
| 5,646,146 A | 7/1997 | Faarup et al. |
| 5,649,547 A | 7/1997 | Ritchart et al. |
| 5,653,718 A | 8/1997 | Yoon |
| 5,665,085 A | 9/1997 | Nardella |
| 5,674,184 A | 10/1997 | Hassler, Jr. |
| 5,676,663 A | 10/1997 | Kim |
| 5,683,384 A | 11/1997 | Gough et al. |
| 5,687,739 A | 11/1997 | McPherson et al. |
| 5,688,490 A | 11/1997 | Tournier et al. |
| 5,715,825 A | 2/1998 | Crowley |
| 5,720,763 A | 2/1998 | Tovey |
| 5,741,225 A | 4/1998 | Lax et al. |
| 5,749,626 A | 5/1998 | Yoshida |
| 5,769,086 A | 6/1998 | Ritchart et al. |
| 5,772,660 A | 6/1998 | Young et al. |
| 5,775,333 A | 7/1998 | Burbank et al. |

(56) References Cited

U.S. PATENT DOCUMENTS

| | | |
|---|---|---|
| 5,782,764 A | 7/1998 | Werne |
| 5,782,775 A | 7/1998 | Milliman et al. |
| 5,794,626 A | 8/1998 | Kieturakis |
| 5,797,907 A | 8/1998 | Clement |
| 5,800,378 A | 9/1998 | Edwards et al. |
| 5,810,806 A | 9/1998 | Ritchart et al. |
| 5,814,044 A | 9/1998 | Hooven |
| 5,846,513 A | 12/1998 | Carroll et al. |
| 5,848,978 A | 12/1998 | Cecchi |
| 5,853,366 A | 12/1998 | Dowlatshahi |
| 5,857,981 A | 1/1999 | Bucalo et al. |
| 5,857,982 A | 1/1999 | Milliman et al. |
| 5,876,340 A | 3/1999 | Tu et al. |
| 5,882,316 A | 3/1999 | Chu et al. |
| 5,902,272 A | 5/1999 | Eggers et al. |
| 5,913,857 A | 6/1999 | Ritchart et al. |
| 5,921,915 A | 7/1999 | Aznoian et al. |
| 5,925,044 A | 7/1999 | Hofmann et al. |
| 5,928,164 A | 7/1999 | Burbank et al. |
| 5,947,964 A | 9/1999 | Eggers et al. |
| 5,954,670 A | 9/1999 | Baker |
| 5,964,716 A | 10/1999 | Gregoire et al. |
| 5,972,002 A | 10/1999 | Bark et al. |
| 5,980,469 A | 11/1999 | Burbank et al. |
| 5,984,919 A | 11/1999 | Hilal et al. |
| 5,997,560 A | 12/1999 | Miller |
| 6,004,269 A | 12/1999 | Crowley et al. |
| 6,036,681 A | 3/2000 | Hooven |
| 6,050,955 A | 4/2000 | Bryan et al. |
| 6,056,700 A | 5/2000 | Burney et al. |
| 6,063,082 A | 5/2000 | DeVore et al. |
| 6,077,179 A | 6/2000 | Liechty, II |
| 6,120,462 A | 9/2000 | Hibner et al. |
| 6,142,955 A | 11/2000 | Farascioni et al. |
| 6,161,034 A | 12/2000 | Burbank et al. |
| 6,220,248 B1 | 4/2001 | Voegele et al. |
| 6,234,177 B1 | 5/2001 | Barsch |
| 6,261,241 B1 | 7/2001 | Burbank et al. |
| 6,277,083 B1 | 8/2001 | Eggers et al. |
| 6,280,399 B1 | 8/2001 | Rossin et al. |
| 6,312,429 B1 | 11/2001 | Burbank et al. |
| 6,331,166 B1 | 12/2001 | Burbank et al. |
| 6,344,026 B1 | 2/2002 | Burbank et al. |
| 6,350,244 B1 | 2/2002 | Fisher |
| 6,387,056 B1 | 5/2002 | Kieturakis |
| 6,419,490 B1 | 7/2002 | Kitchings Weathers, Jr. |
| 6,454,727 B1 | 9/2002 | Burbank et al. |
| 6,478,806 B2 | 11/2002 | McFarlane |
| 6,494,881 B1 | 12/2002 | Bales et al. |
| 6,514,215 B1 | 2/2003 | Ouchi |
| 6,514,248 B1 | 2/2003 | Eggers et al. |
| 6,517,545 B1 | 2/2003 | Mazur |
| 6,540,695 B1 | 4/2003 | Burbank et al. |
| 6,638,234 B2 | 10/2003 | Burbank et al. |
| 6,659,981 B2 | 12/2003 | Stewart et al. |
| 6,679,851 B2 | 1/2004 | Burbank et al. |
| 6,689,145 B2 | 2/2004 | Lee et al. |
| 6,712,775 B2 | 3/2004 | Burbank et al. |
| 6,758,824 B1 | 7/2004 | Miller et al. |
| 7,070,010 B2 | 7/2006 | Papousek |
| 7,189,206 B2 | 3/2007 | Quick et al. |
| 7,201,722 B2 | 4/2007 | Krueger |
| 7,226,424 B2 | 6/2007 | Ritchart et al. |
| 8,343,071 B2 | 1/2013 | Shabaz et al. |
| 9,204,866 B2 | 12/2015 | Shabaz et al. |
| 2003/0004407 A1 | 1/2003 | Carroll et al. |
| 2009/0204021 A1 | 8/2009 | Shabaz et al. |

FOREIGN PATENT DOCUMENTS

| | | |
|---|---|---|
| EP | 0146699 A1 | 7/1985 |
| EP | 0255123 A2 | 2/1988 |
| EP | 0292936 A2 | 11/1988 |
| EP | 0472368 A2 | 2/1992 |
| EP | 0509670 A2 | 10/1992 |
| EP | 0667126 A1 | 8/1995 |
| EP | 0769281 A2 | 4/1997 |
| EP | 0919190 A2 | 6/1999 |
| EP | 0919192 A2 | 6/1999 |
| EP | 0966925 A1 | 12/1999 |
| EP | 0970658 A1 | 1/2000 |
| EP | 0983749 A2 | 3/2000 |
| GB | 2311468 A | 10/1997 |
| JP | H11262490 A | 9/1999 |
| JP | 2001158016 A | 6/2001 |
| JP | 2005530554 A | 10/2005 |
| WO | 9314712 A1 | 8/1993 |
| WO | 9502370 A2 | 1/1995 |
| WO | 9502371 A2 | 1/1995 |
| WO | 9503842 A1 | 2/1995 |
| WO | 9503843 A1 | 2/1995 |
| WO | 9729702 A1 | 8/1997 |
| WO | 9806346 A1 | 2/1998 |
| WO | 9843531 A1 | 10/1998 |
| WO | 9930764 A1 | 6/1999 |
| WO | 0012009 A2 | 3/2000 |
| WO | 0149184 A2 | 7/2001 |
| WO | 0222023 A1 | 3/2002 |
| WO | 02062231 A2 | 8/2002 |
| WO | 02062232 A1 | 8/2002 |
| WO | 2004052212 A1 | 6/2004 |
| WO | 2004075719 A2 | 9/2004 |
| WO | 2005063126 A2 | 7/2005 |
| WO | 2006049911 A1 | 5/2006 |

OTHER PUBLICATIONS

International Search Report for PCT/US2004/043021 dated Apr. 27, 2005.

International Search Report for PCT/US2004/043021 dated Jul. 26, 2005.

Written Opinion of the International Searching Authority for PCT/US2004/043021 dated Jul. 26, 2005.

International Search Report for PCT/US2005/027071 dated Mar. 21, 2006.

International Search Report for PCT/US2005/027071 dated Jul. 5, 2006.

Written Opinion of the International Searching Authority for PCT/US2005/027071 dated Feb. 3, 2007.

Storm, et al., "Clinical Thermochemotherapy, A Controlled Trial in Advanced Cancer Patients", Cancer, Feb. 15, 1984, pp. 863-868, vol. 53.

Doss, et al., "HDR Brachytherapy for Osteolytic Metastases in Previously Irradiated Sites", International Brachytherapy, Chapter 101, Sep. 1992, pp. 412-415, Memorial Regional Cancer Center, Modesto, CA.

Kuske, et al. "Brachytherapy as Sole Method for Early Breast Cancer", International Brachytherapy, Chapter 80, pp. 347-348, Ochsner Medical Institutions, New Orleans, Louisiana.

Desinger, et al., "A New Application System for Simultaneous Laser and Ultrasonic Transmission in Endoscopic Surgery (LUST)", Surgical Applications of Energy, 94, vol. 3249 Apr. 2, 1998, San Jose, CA.

Desinger, et al., "Interstitial bipolar RF-thermotherapy (RFITT) Therapy planning by computer simulation and MRI-monitoring—A new concept for minimally invasive procedures—" Surgical Applications of Energy, 147, vol. 3249, Apr. 2, 1998, San Jose, CA.

"The Dangers of Monopolar Electrosurgery and The Advantages of Bipolar Electrosurgery", Everest Medical, Technical Reviews; www.pycco.com/emc/techrvws.html, May 26, 1998, pp. 1-9.

Hausner, K, "Laser Vs Electrosurgery", www.netvs.com/elmed/lasvselec.htm, May 19, 1998, pp. 1-4.

Bown, S. G., "Phototherapy of Tumors", World Journal of Surgery, 1983, vol. 7, pp. 700-709, University College Hospital, London, United Kingdom.

Jacques, et al., "Liver photocoagulation with diode laser (805 nm) vs Nd:YAG laser (1064 nm)", SPIE vol. 1646 Laser-Tissue Interaction III 1992, pp. 107-125.

(56) References Cited

OTHER PUBLICATIONS

Jolesz, et al., "MR Imaging of Laser-Tissue Interactions", Magnetic Resonance Imaging, Radiology, Jul. 1988; pp. 249-253, vol. 168.
Anzai, et al., "Nd:YAG Interstitial Laser Phototherapy Guided by Magnetic Resonance Imaging in an Ex Vivo Model: Dosimetry of Laser-MR-Tissue Interaction", Laryngoscope 101: Jul. 1991, pp. 755-760.
Le Bihan, et al., "Temperature Mapping with MR Imaging of Molecular Diffusion; Application to Hyperthermia", Therapeutic Radiology, Radiology, Jun. 1988, pp. 853-857, vol. 171.
Masters, et al., "Interstitial Laser Hyperthermia In Tumour Therapy", Annales Chirugiae et Gynaecologiae 79:244-251, 1990.
Harries, et al., "Interstitial laser photocoagulation as a treatment for breast cancer", British Journal of Surgery 1994, 81, 1617-1619.
"Ultrasound-Guided Cryosurgery for Tumor Ablation", Mar. 22, 1995, Sheraton Boston Hotel & Towers, Boston, MA, Sponsored by: Deconess Hospital.
Gehman, et al., "High Dose Rate Endovascular Irradiation; Tolerance of Normal Tissues", Endocurietherapy/Hyperthermia Oncology, Jul. 1994, vol. 10, pp. 167-171, ISSN 8756-1687.
Bottcher, et al. "Endovascular Irradiation—A New Method To Avoid Recurrent Stenosis After Stent Implantation In Peripheral Arteries: Technique and Preliminary Results", 34th Annual ASTRO Meeting, San Diego, CA, Nov. 1992, International Journal of Radiation Oncology Biol. Phys., vol. 29, No. 1, pp. 183-186, 1994.
Fletcher, G. H., "Textbook of Radiotherapy" Third Edition, Lea & Febiger, 1980, Philadelphia.
Cox, J. D., "Moss' Radiation Oncology: Rationale, Technique, Results" Seventh Edition, Mosby 1994.
Amin, Zehir, MRCP et al., "Hepatic Metastases: Interstitial Laser Photocoagulation with Real-Time US Monitoring and Dynamic CT Evaluation of Treatment", Radiology, May 1993; vol. 187, pp. 339-347.
Armstrong, J.S. et al., "Differential marking of excision planes in screened breast lesions by organically coloured gelantins", Journal of Clinical Pathology, (Jul. 1990), 43(7) 604-7, XP000971447 abstract; tables 1 and 2.
Burbank, F., M.D., Stereotactic Breast Biopsy: Its History, Its Present, and Its Future, The American Surgeon, Feb. 1996, vol. 62, pp. 128-150.
Fucci, V. et al., "Large Bowel Transit Times Using Radiopaque Markers in Normal Cats", J. Of Am. Animal Hospital Assn., Nov.-Dec. 1995 Vol. 31 (6) 473-477.
Lorenzen,T. et al., The Loop Electrode: a New Device for US-guided Interstitial Tissue Ablation Using Radio frequency Electrosurgery—An Animal Study, 1996 Blackwell Science Ltd. Min Invas Ther & Allied Technol, pp. 5.511-516.
Micklos, Timothy J., Percutaneous Biopsy Techniques, Manual of Oncologic Therapeutics (1989/1990) pp. 39-42.
Nolsoe, Christian P., et al., "Interstitial Hyperthermia of Colorectal Liver Metastases with a US-guided Nd-YAG Laser with a Diffuser Tip: A Pilot Clinical Study", Radiology, May 1993, vol. 187, pp. 333-337.
Schindlebeck, N. E., et al., "Measurement of Colon Transit Time", J. of Gastroenterology, No. 28, pp. 399-404, 1990.
Canavan, et al., Dr. F., "Vaccuum Assisted Breast Biopsy: A Comparison of 3 Systems", Presentation poster, Kings College Hospital NHS Foundation Trust; Aug. 2008.
Whitman, et al., Coaxial Core Needle Biopsy Under Mammographic Guidance: Indications and Applications, AJR:171, Jul. 1998, pp. 67-70.

BIOPSY DEVICE WITH APERTURE ORIENTATION AND IMPROVED TIP

RELATED APPLICATIONS

This application is a continuation of application Ser. No. 13/747,530, filed Jan. 23, 2013, now U.S. Pat. No. 10,105,125, which is a continuation of application Ser. No. 11/981,024, filed Oct. 31, 2007, now U.S. Pat. No. 8,360,990, which is a division of application Ser. No. 11/014,413, filed Dec. 16, 2004, now U.S. Pat. No. 9,408,592. Priority is based on these applications and these applications are incorporated herein in their entirety.

FIELD OF THE INVENTION

The present invention relates generally to tissue removing devices such as biopsy devices and the methods of using such devices. More specifically, it is directed to an improved device and method for accessing and removing pathologically suspect tissue from within a patient's body.

BACKGROUND OF THE INVENTION

In diagnosing and treating certain medical conditions, such as potentially cancerous tumors, it is usually desirable to perform a biopsy, in which a specimen of the suspicious tissue is removed for pathological examination and analysis. In many instances, the suspicious tissue is located in a subcutaneous site, such as inside a human breast. To minimize surgical intrusion into the patient's body, it is desirable to be able to insert a small instrument into the patient's body to access the targeted site and to extract the biopsy specimen therefrom.

Electrosurgical techniques have been used in a variety of biopsy procedures. In electrosurgery, high frequency electrical energy is typically applied to patient tissue through an active electrode, the electrical circuit being completed by a return electrode in contact with the patent's tissue. Electrical energy flowing through the tissue from the active electrode is effective to ablate tissue near the active electrode, forming an opening in the tissue and so allowing insertion of the instrument into a patient's body. A return electrode may be placed on the exterior of the patient's body or may be incorporated into the device itself. The return electrode is typically attached to the patient at a point remote from where the primary or active electrode contacts the tissue. However, in the case of a bipolar electrode for example, the return electrode may be disposed near to the active electrode. An electrosurgical biopsy instrument is disclosed and claimed in U.S. patent application Ser. No. 09/159,467 for "Electrosurgical Biopsy Device and Method," now U.S. Pat. No. 6,261,241, assigned to the assignee of the present application, and which is hereby incorporated by reference in its entirety. A variety of needle like tip designs have been developed to aid in the accessing of intracorporeal sites for biopsy and other procedures. Electrosurgical techniques have also been used in a variety of biopsy procedures to gain access to an intracorporeal site. See for example U.S. Pat. No. 6,261,241, assigned to the assignee of the present application, and which is hereby incorporated by reference in its entirety.

The prior needle like tips do not always allow proper placement of the biopsy or other surgical device. Moreover, while the electrosurgical biopsy devices have been found to be effective in many instances, they are not suitable for use in conjunction with magnetic resonance imaging.

While these electrosurgical biopsy devices have been found to be effective in many instances, they may not always be suitable for use in conjunction with magnetic resonance imaging.

SUMMARY OF THE INVENTION

This invention is directed to devices for accessing and severing tissue from a target site within a patient and methods for utilizing such devices. The devices embodying features of the invention provide access to a targeted tissue site within a patient and provide for the selection, separation and capture of a tissue specimen from supporting tissue at the targeted site.

A tissue accessing and severing device and system having features of the invention generally include an elongated, preferably disposable probe component having a plurality of operative elements and a driver component configured to receive the elongated probe component and drive the various operative elements of the probe component.

The elongated probe component has a distal shaft portion with a tissue penetrating distal tip, a tubular section proximal to the distal tip, an inner lumen extending within the tubular section and an open, tissue receiving aperture in the tubular section which provides access to tissue at the targeted site. The probe component includes an elongated tissue-cutting member, which is preferably at least in part cylindrically shaped. The tissue cutting member is provided with at least one tissue cutting edge which is configured to sever tissue extending into the interior of the tubular section through the aperture thereof. The cutting edge on the tissue cutting member may be configured for longitudinal cutting movement and may include oscillating rotational motion and/or reciprocating longitudinal motion to sever specimen tissue extending through the aperture from supporting tissue at the targeted site. The cutting surfaces or edges are radially spaced from a longitudinal axis of the probe component and are generally transversely oriented with respect to the longitudinal axis. The tissue cutter is preferably slidably disposed within the inner lumen of the tubular section, although it may be disposed about the tubular section. The probe component may also have a handle which releasably engages the driver component.

In one embodiment of the invention, the cutting member has an inner lumen preferably extending to the proximal end thereof for tissue specimen removal. While mechanical withdrawal of the tissue specimen may be employed, it is preferred to provide a vacuum within the cutting member from the proximal end of the cutting member. The proximal end of the cutting member may be configured to be in fluid communication with a vacuum source to aspirate the severed tissue specimen through the inner lumen of the cutting member to a tissue collection station. A higher fluid pressure may be maintained in the inner lumen of the cutting member distal to the tissue specimen to aid in transporting the specimen proximally through the inner lumen. In this manner, the mechanical withdrawal and/or the vacuum on the proximal end of the specimen and a higher pressure on the distal end of the specimen can move the specimen through the inner lumen of the cutting member to a tissue collection station.

In at least one embodiment, the handle of the probe component is secured, preferably releasably secured, to the driver housing provided to operably connect the various operative elements of the probe with operative elements of the driver component. The tissue cutting member is operatively connected to at least one driver to provide the desired cutting motion. The proximal end of the tubular section is rotatably secured within the handle housing so that the orientation thereof with respect to the longitudinal axis and therefore the orientation of the tissue receiving aperture within the tubular section, can be selected. The orientation of the aperture may be selected manually such as described in copending application Ser. No. 10/642,406, filed February Aug. 15, 2003 or it may be preset or selected electronically by a control module which also controls the operation of the cutting member and electrical power. The aperture orientation setting may be selected before or after the distal portion of the probe component is inserted into the patient.

The tissue penetrating distal tip embodying features of the invention has a proximal base secured to the distal end of the probe shaft of the biopsy device, and a sharp distal point distal to the proximal base. The tissue penetrating distal tip has a first concave surface extending from the base to the sharp distal point. The distal tip also has a second concave surface, which intersects the first concave surface forming therewith a first curved cutting edge that leads to the sharp distal point. The distal tip also has a third concave surface which intersects the first concave surface forming therewith a second curved cutting edge leading to the sharp distal point and also intersects the second concave surface forming therewith a third curved cutting edge that leads to the sharp distal point. The concave surfaces preferably have center lines which extend from the proximal base of the distal tip to the sharp distal point. In a presently preferred embodiment the concave surfaces are of the same area. However, they may have different areas.

The driver component has at least two and preferably three driver units for operating the probe component secured to the driver component. Specifically, the driver component has a first driver unit for rotating the tubular section of the probe component, a second driver unit for moving the cutting member along a longitudinal axis of the cutting member and optionally a third driving unit for rotating or oscillating the cutting member about the longitudinal axis. The first driver unit rotates the tubular section of the probe component, preferably in discrete steps, so that the location of the tissue receiving aperture in the distal extremity of the tubular section can be selected prior to or during the procedure. The discrete rotational steps of the tubular section are preferably in 30° or multiples thereof so that the rotational movement will follow 12 hour clock markings. Preferably, the second and third driver units are operable together so that the cutting member may rotate or oscillate about a longitudinal axis as the cutter member is moved longitudinally. This allows a rotation or an oscillation of the cutter during the cutting process which can aid in cutting tissue.

The driver component may have one or more light sources in a distal portion thereof to illuminate the accessing site during the procedure.

A method of cutting and collecting a tissue specimen with a tissue collection device embodying features of the invention includes advancing such a device at least partially into tissue at a desired site within the patient's body with the tissue penetrating distal tip of the outer cannula disposed distal to the tissue specimen to be separated from the target site. A vacuum is established within the inner lumen of the tubular section to draw tissue through the aperture therein into the inner lumen of the tubular section. The cutting member, which is slidable disposed within the inner lumen of the tubular section, may then be moved longitudinally to cut a tissue specimen from supporting tissue at the target site by the longitudinal motion, which preferably includes oscillating rotational movement and/or reciprocating longitudinal movement. The vacuum established within the inner lumen of the tubular section may be applied through the inner lumen of the tissue cutting member when the tissue cutting member is disposed within the tubular section. The applied vacuum within the inner lumen of the tissue cutting member, may also be utilized to pull or aspirate the separated tissue sample proximally. In addition, or alternatively, a higher fluid pressure may be maintained in a distal part of the inner lumen of the tubular section, distal to the specimen, to push the tissue specimen proximally, Alternatively, the tissue specimen may be mechanically withdrawn. Fluid pressure may include pressure from a liquid delivered into the interior of the device, such as a physiological saline solution, and may include a gas, such as pressurized carbon dioxide, nitrogen or air, delivered into the interior of the device. Access to ambient air can also maintain a sufficiently high pressure differential to move the specimen through the inner lumen of the cutting member. Anesthetic may be injected to the target site through the outer cannula or the inner lumen of the cutting member. Upon removal from the patient, the tissue specimen may then be subjected to pathological examination. After acquisition of a tissue specimen or specimens, the tissue separation system may be repositioned for further tissue separation and collection or it may be withdrawn from the patient.

The tubular section of the probe provides the support for the probe to enable precise location of the accessing port to the desired location at the target site with its radial orientations being preset before the device is introduced into the patient or selected after the tubular section is disposed within the patient. The cutting member quickly and cleanly severs the tissue specimen drawn into the interior of the tubular section though the aperture by the action of the vacuum or otherwise. Upon removal of the tissue specimen, the tissue receiving aperture may be radially repositioned about the longitudinal axis of the tubular section of the probe component so that a plurality of specimens may be taken from the target site. The orientation of the tissue receiving aperture during the procedure may follow a preselected pattern or may be selected by the physician for other selected tissue specimens.

A tissue acquisition system assembly embodying features of the invention may include a device for delivery of one or more marker bodies through a tubular member of a biopsy device such as the tubular cutting member. Such a marker delivery device includes an elongated shaft having an inner lumen and a discharge opening in a distal portion of the elongated shaft, at least one marker body which is disposed within the inner lumen of the elongated shaft, a pusher element which is slidably disposed within the delivery device and which is configured to urge at least one marker body out the discharge opening in the distal portion of the elongated shaft. The marker delivery device has a distally flared guide member which is slidably disposed on the elongated shaft to guide the distal portion of the elongated shaft into a proximal end of the tubular member of a biopsy device. This invention is directed to a tissue penetrating probe tip, particularly for biopsy devices. These devices provide access to a targeted tissue site and provide for the separation and capture of a tissue specimen from supporting tissue at the targeted site.

These and other advantages of the invention will become more apparent from the following detailed description of the invention and the accompanying exemplary drawings.

DETAILED DESCRIPTION OF EMBODIMENTS OF THE INVENTION

Figure 1:
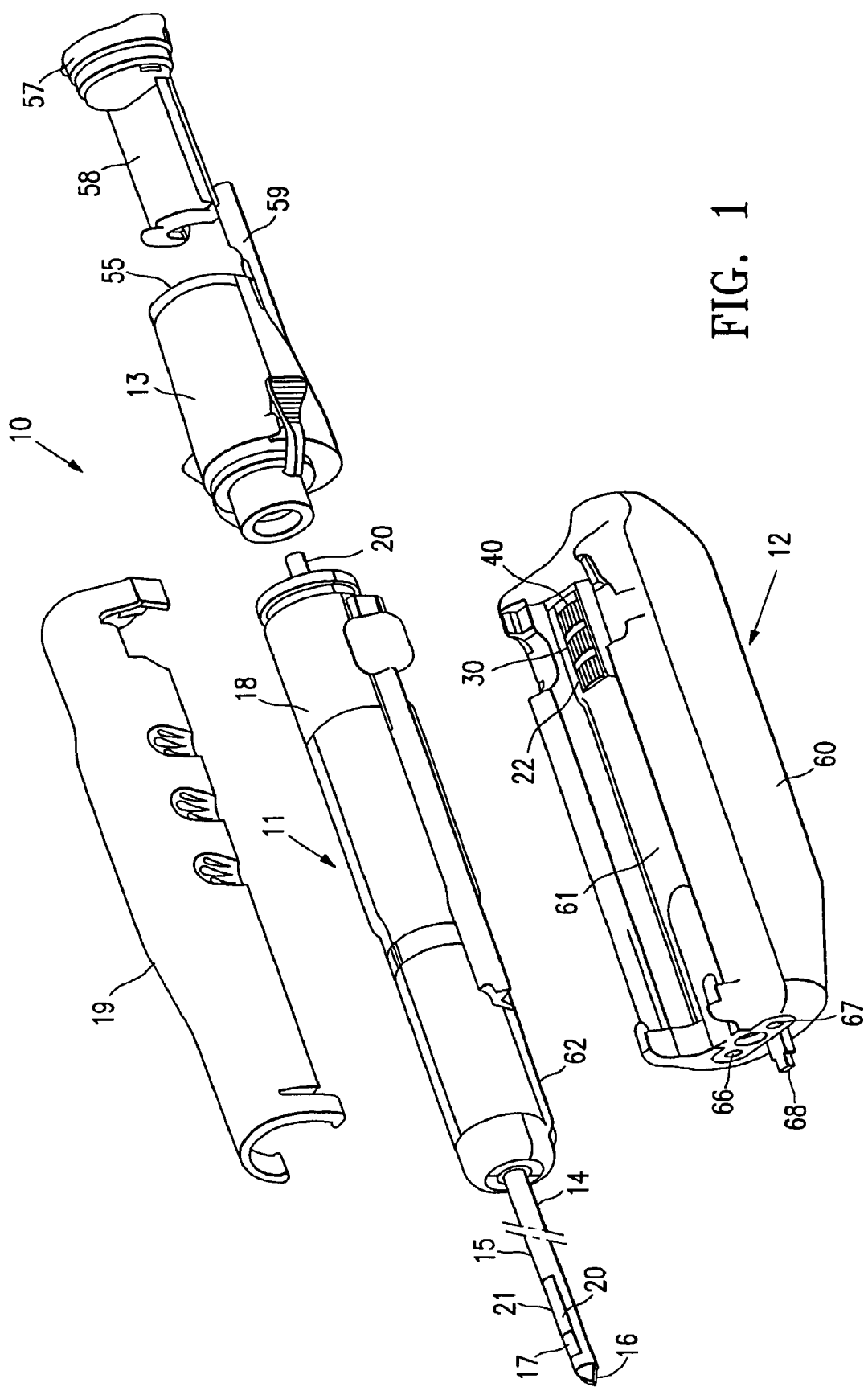
FIG. 1 is an exploded view of the elongated tissue biopsy system embodying features of the invention.
Figure 2:
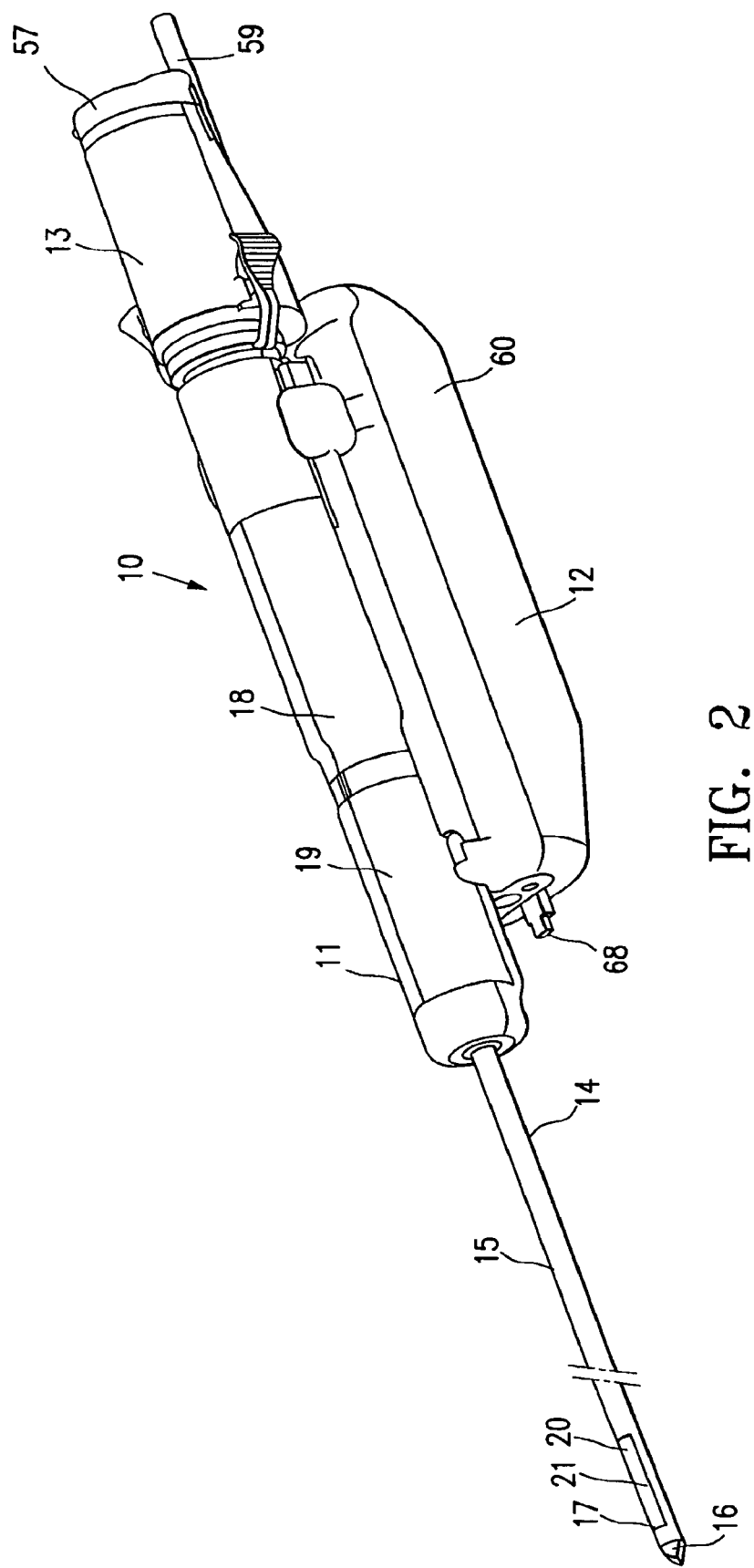
FIG. 2 is a perspective view of the embodiment shown in FIG. 1 in an assembled condition without a housing cover for the probe component.
Figure 3:
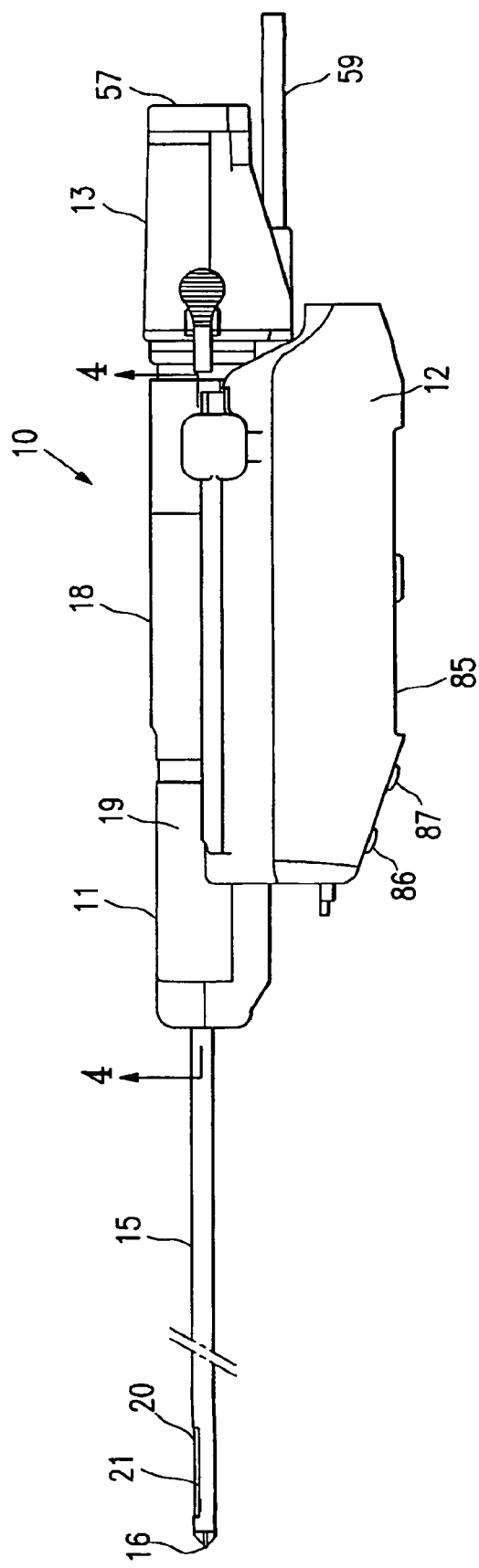
FIG. 3 is a side elevational view of the tissue biopsy device shown in the FIG. 2.

FIGS. 1-3 illustrate a biopsy system 10 embodying features of the invention which includes a disposable probe component 11, a driver component 12 and specimen collector 13.

The probe component 11 generally includes an elongated distal shaft 14 having a tubular section or cannula 15 with a tissue penetrating tip 16 on the distal end thereof and an open, tissue receiving aperture 17. The probe component 11 also includes a probe housing 18 with a housing cover 19 which is configured to interfit with the driver component 12. A tissue cutter 20 is slidably disposed within the probe and has a distal cutting surface 21 which severs tissue which extends through the tissue receiving aperture 17.

Figure 4A:
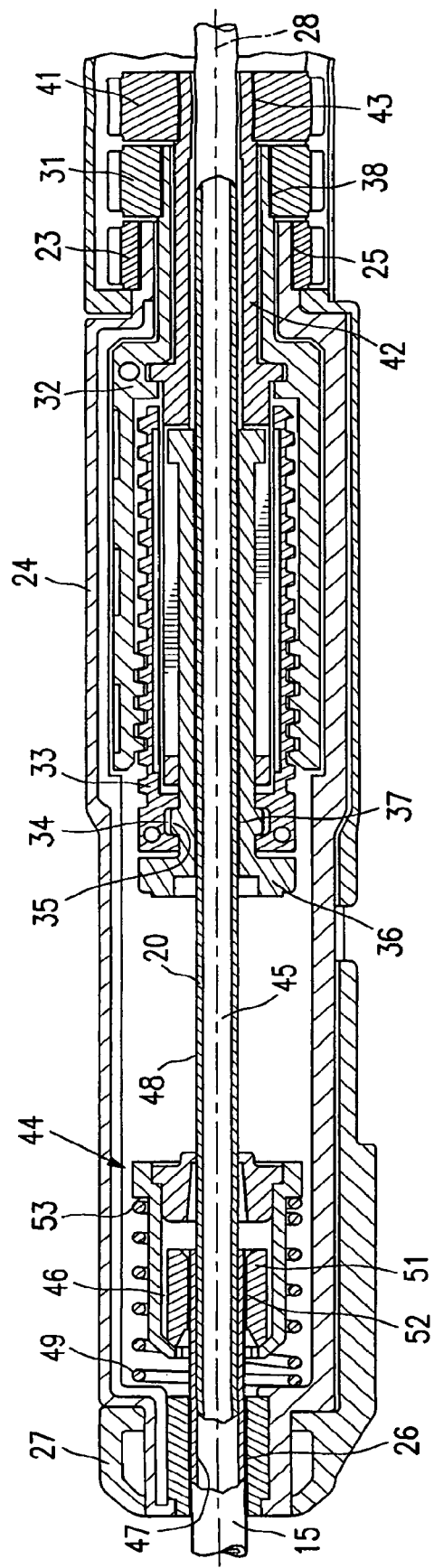
FIG. 4A is a longitudinal cross-section of the probe shown in FIG. 3 taken along the lines 4-4 with the tissue cutting element in a withdrawn position.
Figure 4B:
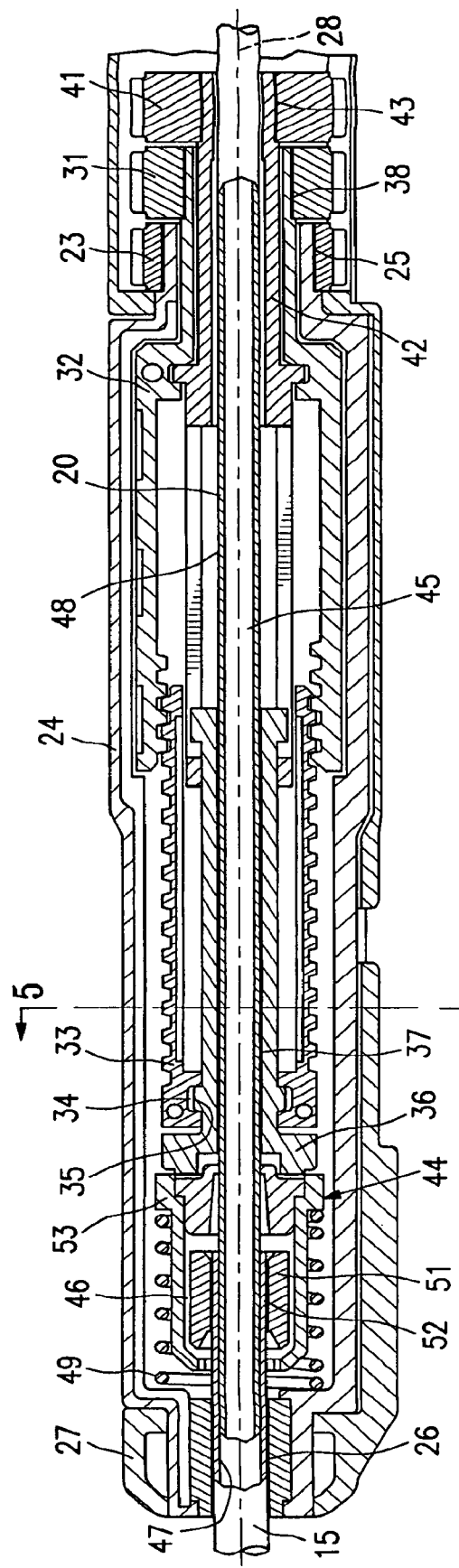
FIG. 4B is a longitudinal cross-section of the probe shown in FIG. 3 taken along the lines 4-4 with the tissue cutting element in a forward or closed position.
Figure 5:
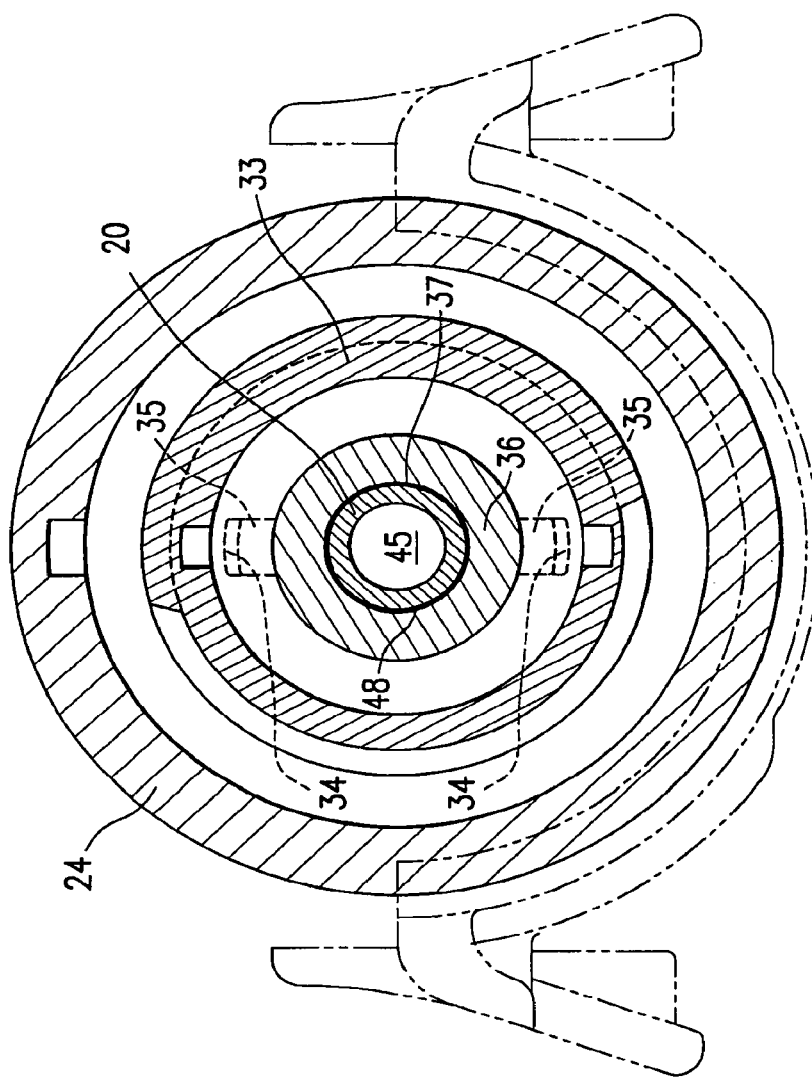
FIG. 5 is a transverse cross-sectional view of the probe shown in FIG. 4B taken along the lines 5-5.
Figure 6:
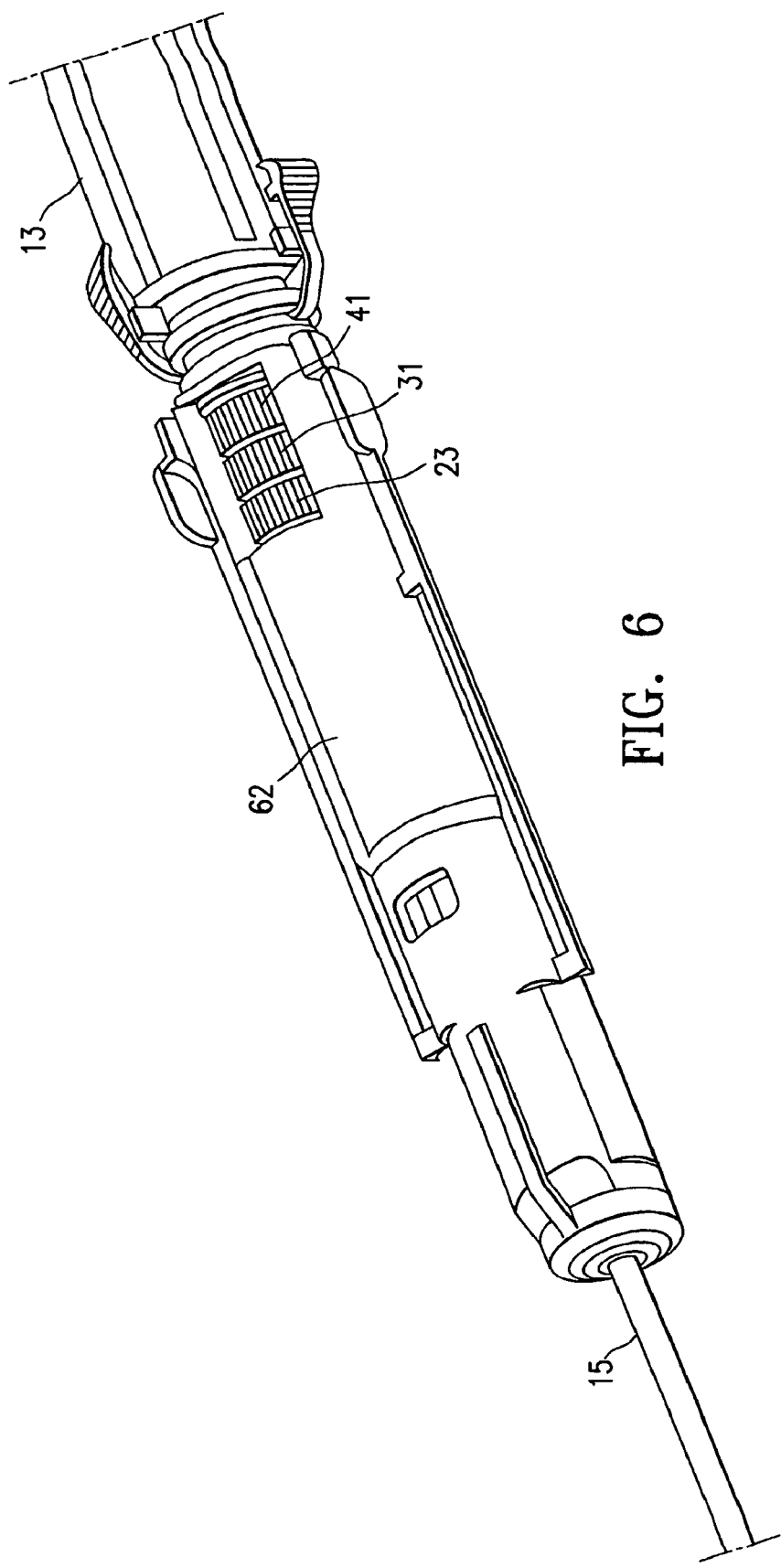
FIG. 6 is a perspective view of the underside of the probe shown in FIG. 1.

Details of the probe component 11 are further shown in FIGS. 4A and 4B. The probe housing 18 has a mechanical system for rotating the housing and the tubular section 15 secured thereto to control the angular position of the tissue receiving aperture 17 and for moving the tissue cutter 20 slidably disposed within the probe component 11.

Figure 8:
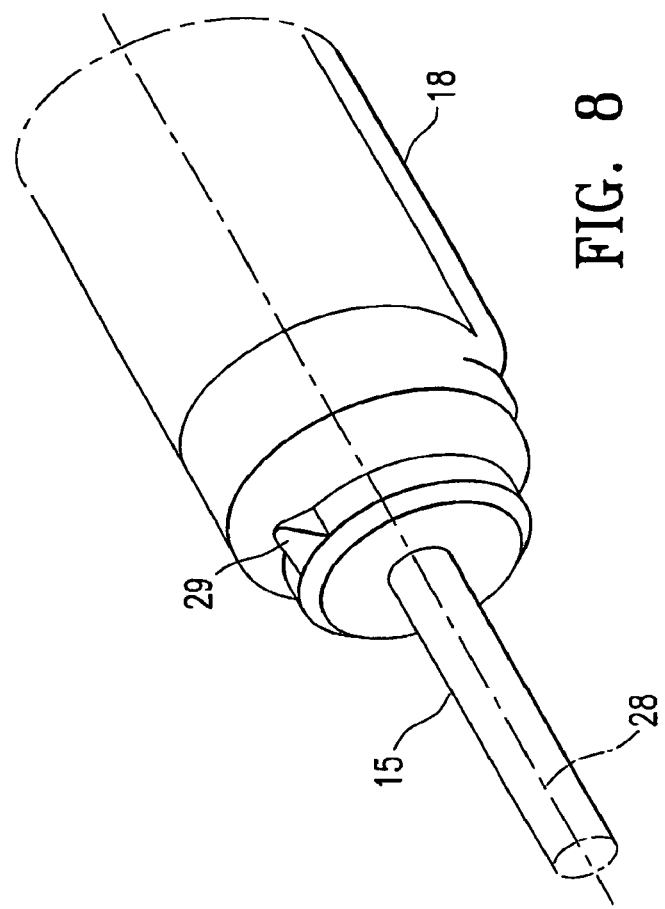
FIG. 8 is an enlarged perspective view of the distal end of the probe housing illustrating a marker element which depicts the orientation of the aperture in the tubular section of the biopsy device.

The mechanical system of the driver component 12 has first driving gear 22 that is configured to engage the probe gear 23 and rotate the probe housing 18 so as to adjust the orientation of aperture 17 in the distal extremity of the tubular section 15. The probe gear 23 is secured to the rotating connector body 24 by adhesive 25. The proximal extremity of the tubular section 15 is secured to the rotating connector body 24 by adhesive 26. An end cap 27 retains the connector body 24 within the probe housing 18. Rotation of the probe gear 23 rotates the connector body 24 and the attached tubular section 15. The rotation is preferably controlled so that the tubular section 15 rotates in discrete steps about the longitudinal axis 28 to adjust the angular orientation of the aperture 17 about the longitudinal axis. Preferably these discrete orientations may be provided in increments of 30° which can be readily indicated by arrow 29 at the distal end of the probe housing 18 as shown in FIG. 8.

The second driving gear 30 is configured to drive the tissue cutter 20 longitudinally. The driving gear 30 engages probe gear 31 which drives cutter traverse nut 32 and cutter screw 33 threadably connected to the cutter traverse nut. The distal end of the cutter screw 33 is provided with a recess 34 which receives the rib 35 of the cutter shuttle 36. The cutter shuttle 36 is secured to the tissue cutter 20 by adhesive 37. The probe gear 31 is secured to the cutter traverse nut 32 by adhesive 38. Rotation of the probe gear 31 adjusts the relative axial position of the cutter screw 33 with respect to the cutter traverse nut 32 which is secured to the cutter shuttle 36. Longitudinal movement of the tissue cutter 20 follows the longitudinal movement of the cutter shuttle 36 resulting from the movement of cutter screw 33. The length of the tissue receiving aperture 17, and as a result the length of the specimen, can be controlled by adjusting the initial longitudinal position of the distal end of the tissue cutter 20 within the aperture, before cutting.

The third driving gear 40 is configured to rotate or oscillate the tissue cutter 20 as the cutter moves along the longitudinal axis 28 to facilitate the cutting action of the cutting surface 21 on the distal end of the cutter. The third driving gear 40 engages probe gear 41 which is secured to cutter oscillation shaft 42 by adhesive 43. The probe gear 41 may be oscillated back and forth about the longitudinal axis 28 or rotated continuously in a single direction about the longitudinal axis, or both depending upon the desired rotational movement of the tissue cutter.

A biased valve assembly 44 is provided in the distal end of the probe housing 18 to ensure sealing when a vacuum is developed within the interior 45 of the tissue cutter 20 while providing an atmospheric vent 46 between the interior surface 47 of the tubular section 15 and the exterior surface 48 of the tissue cutter 20. The valve assembly 44 includes a spring 49, valve body 50 and a valve collar 51 which is secured to the proximal end of the tubular section 15 by adhesive 52. The proximal end of the valve spring 49 rests against the shoulder 53 provided in the exterior of the valve body 50. A biased cutter shaft seal 54 slidably engages the exterior 48 of the tissue cutter 20.

The tissue specimen collector 13 is secured to the proximal end of the housing of probe component 11 and has an interior 55 in fluid communication with the inner lumen 56 extending within the tissue cutter 20 and has a removable proximal wall 57 of specimen receiving cartridge 58 which gives access to the interior 55 and any tissue specimens which may have been drawn therein. A vacuum is generated within the interior 55 to draw tissue specimens through the inner lumen 45 into the interior 55. Tubular member 59 has a distal end which is in fluid communication with the interior 55 of the tissue specimen collector 13 and has a proximal end (not shown) which is configured to be connected to a vacuum source. Application of a vacuum within the tubular member 59 aids in pulling tissue into the interior 17 of the tubular section 15 and transfer of the severed tissue specimen through the inner lumen 45 of the tissue cutter 20 to the specimen cartridge 58.

The driver 12 has a housing 60 with an upper concave surface 61 which is configured to receive the lower surface 62 of the probe housing 18. Three partially exposed driving gears 22, 30 and 40 are provided on the proximal end of the driver 12 which are configured to engage the probe gears 23, 31 and 41 respectively. The drive 12 is provided with three separately operating drive motors (not shown) which drive the drive gears 22, 30 and 40. The separate drive motors (not shown) are connected to and the operation thereof controlled by a control module, such as described in copending application Ser. No. 10/847,699, filed on May 17, 2004. The control module controls the motors which move the individual drive gears 22, 30 and 40. The gear 22 engages gear 23 in the probe 11 to control the rotation of the probe housing 18 and the location and orientation of the tissue receiving aperture 17. The drive gear 30 engages probe gear 31 to control the longitudinal position and motion of the tissue cutter 20 along the longitudinal axis 28. Drive gear 40 engages probe gear 41 to control the oscillation or rotation of the tissue cutter 20 about the longitudinal axis 28.

Figure 7:
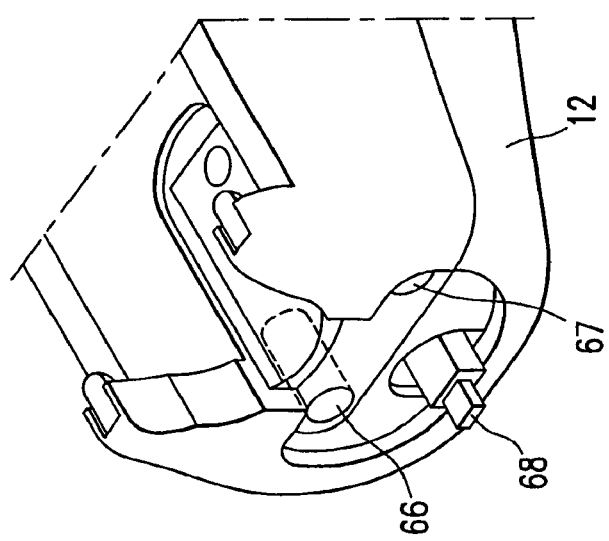
FIG. 7 is an enlarged perspective view of the distal end of the driver unit shown in FIG. 1.
Figure 9:
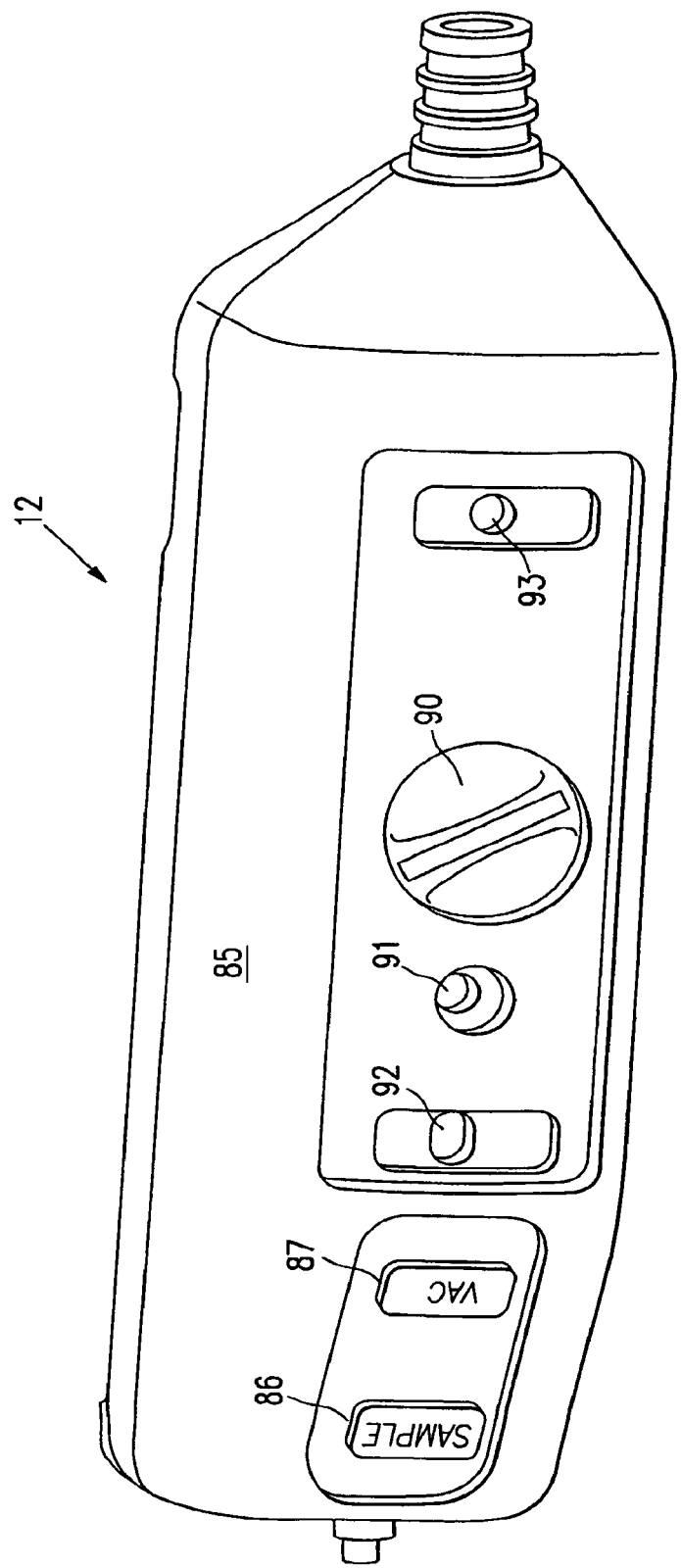
FIG. 9 is a perspective view of the underside of the driver shown in FIG. 1.

As shown in FIG. 7, the front face of the driver component 12 is provided with light sources 66 and 67 and a manually activatable switch 68 to activate the light sources and enable the physician and other operating personnel to better view the operating site on the patient. Other manual switches, e.g. a foot activated switch, may be employed. Alternatively, the light sources may be automatically activated when the probe component 11 is installed on the driver 12 or other events such as when electrical power is turned on. The driver component 12 may have a battery pack for the light sources 66 and 67.

The tissue penetrating distal tip 16 may have a variety of tip shapes. A particularly suitable distal tip embodying features of the invention is shown in FIGS. 9-20. The tissue penetrating distal tip generally includes a base 70, a sharp distal point 71, a first concave surface 72, a second concave surface 73 and a third concave surface 74.

The intersection between the first concave surface 72 and the second concave surface 73 forms the first curved cutting edge 75. The intersection between the second concave surface 73 and the third concave surface 74 forms the second curved cutting edge 76. The intersection between the third concave surface and the first concave surface 72 forms the third curved cutting surface 77.

The concave surfaces 72, 73 and 74 are hollow ground and the pentrating tip 16 is then electro-polished to increase the sharpness of the cutting edges 75, 76 and 77. The penetrating distal tip 16 may be formed of suitable surgical stainless steel such as 17-4 stainless steel. Other materials may be suitable. The penetrating distal tip 16 is preferably electro-polished in an acidic solution to sharpen the curved cutting edges and thereby facilitate tissue penetration. Suitable electro-polishing solutions include Electro Glo sold by the Electro Glo Distributing Co.

The base 70 of the tissue penetrating tip 16 may be secured to the distal end of the elongated shaft of the biopsy device 10 for accessing and collecting tissue from a target site within a patient. The sharp distal tip 16 embodying features of the invention readily penetrates a patient's tissue, particularly breast tissue and facilitates guiding the distal end of the biopsy or other device to a desired intracorporeal location.

The tissue penetrating tips may also be employed on biopsy devices such as those described in co-pending application Ser. No. 10/642,406, filed on Aug. 15, 2003, which is assigned to the present assignee. Alternatively, the distal tip may be provided with an arcuate RF electrode such as disclosed in U.S. Pat. Nos. 6,261,241, and 6,471,700, both assigned to the present assignee.

The separate driver component 12 allows the probe unit 11 to be disposable. The drive gears of the drive component 12 control the motion of the tissue cutting member 20 for cutting and the motion of the tubular section 15 to orient the aperture 17. Other means (not shown) may provide mechanical and electrical power, vacuum, and control to the probe device. Examples of replaceable snap-in type probe units are disclosed in Burbank et al., U.S. patent application Ser. No. 10/179,933, "Apparatus and Methods for Accessing a Body Site". Drive units such as that described in WO 02/069808 (which corresponds to co-pending U.S. application Ser. No. 09/707,022, filed Nov. 6, 2000 and U.S. application Ser. No. 09/864,021, filed May 23, 2001), which are assigned to the present assignee, may be readily modified by those skilled in the art to accommodate the movement of the cutting member 20.

In use, the distal end of the probe component 11 is advanced within the patient with the tissue cutter 20 in a forward or closed position (FIG. 4B), until the aperture 17 of the tubular section 15 is located in a desired location for taking a tissue specimen. The tissue cutter 20 is then withdrawn proximally to an open position to open the aperture 17. The withdrawal of the tissue cutter can be used to control the length of the aperture which is opened in order to control the length of the specimen which is severed. A vacuum is applied to the interior 45 of the tissue cutter 20 to draw tissue at the site into the inner lumen of the tubular section 15 through the aperture 17. The tissue cutter 20 is then driven distally by rotation of probe gear 30 and rotated or oscillated by drive gear 40 engaging probe gear 41 to sever the aspirated tissue from the supporting tissue at the target site with the tissue cutting surface 21. The vacuum within the interior of the tissue cutter 20 causes the tissue specimen to be drawn through the inner lumen 45 of the tissue cutter 20 and into the cartridge 58 of specimen collector 13 shown in FIG. 2. Positive pressure or even ambient conditions distal to the tissue specimen can facilitate tissue passing through the interior 45 of tissue cutter 20. If another tissue specimen is desired, the tubular section 15 may be rotated by the drive gear 22 engaging the probe gear 23 in one or more steps to repeat obtaining another tissue specimen in the same manner without otherwise moving the probe component 11. Typically, a first tissue specimen is obtained with the aperture 17 of the probe 11 in the 12 o-clock position, the second at the 3 o-clock position, the third at the 9 o-clock position and the fourth at the 6 o-clock position. The location of the second and third specimens may be reversed. The position of the aperture 17 may be indicated by a marker arrow 29 at the end cap 27 so that the physician or other operating personnel can readily determine what the orientation of the aperture 17 within the patient.

Figure 10:
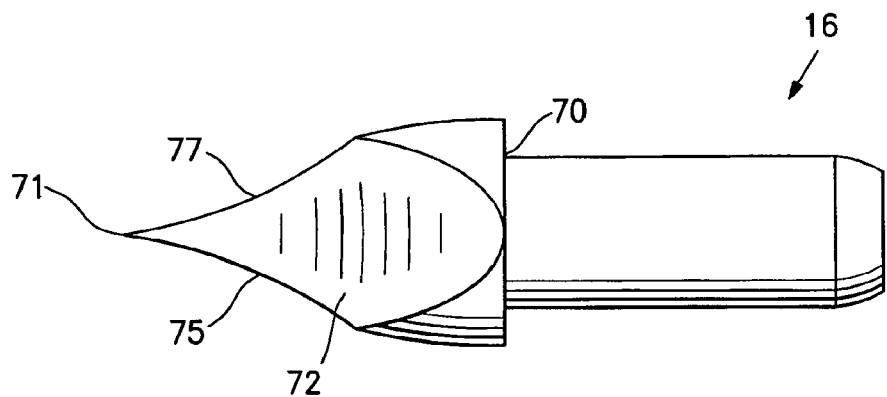
FIG. 10 is an elevational view of a tissue penetrating tip embodying features of the invention.
Figure 11:
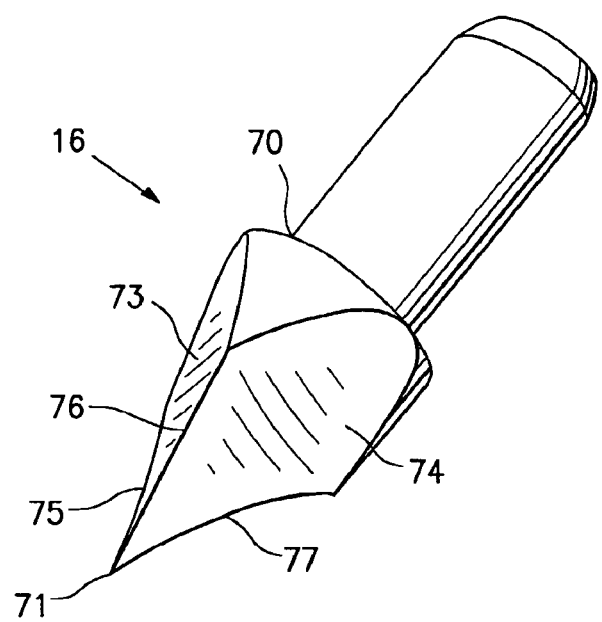
FIG. 11 is a perspective view of the underside of the tip shown in FIG. 10.
Figure 12:
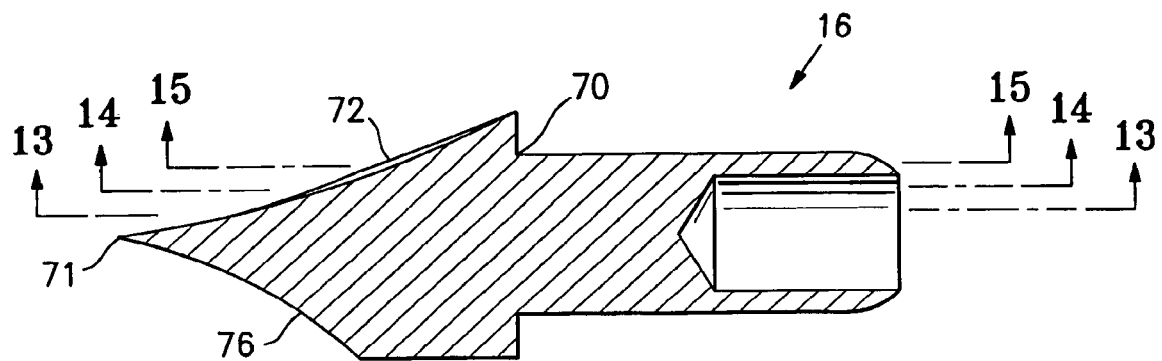
FIG. 12 is a longitudinal, center line cross-sectional view of the penetrating tip shown in FIG. 10.
Figure 13:
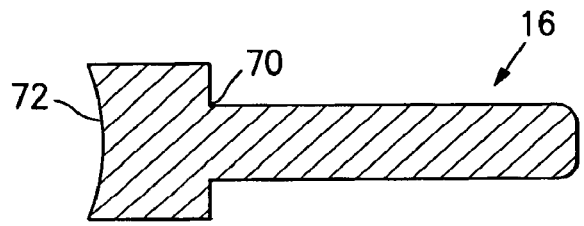
FIG. 13 is a longitudinal cross-sectional view of the penetrating tip shown in FIG. 12 taken along the lines 13-13.
Figure 14:
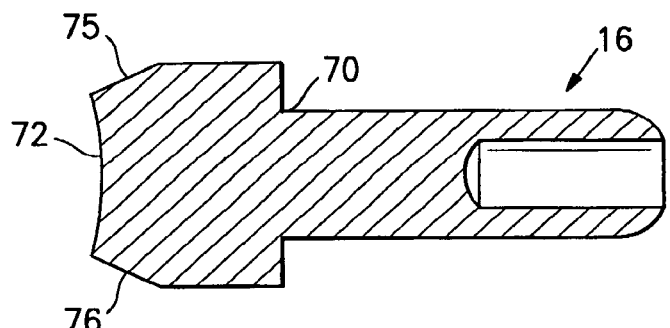
FIG. 14 is a longitudinal cross-sectional view of the penetrating tip shown in FIG. 12 taken along the lines 14-14.
Figure 15:
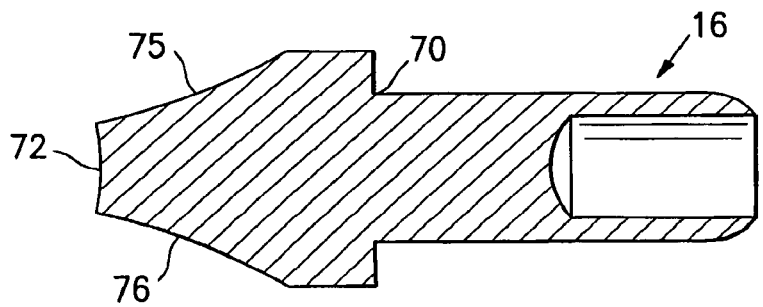
FIG. 15 is a longitudinal cross-sectional view of the penetrating tip shown in FIG. 3 taken along the lines 15-15.
Figure 16:
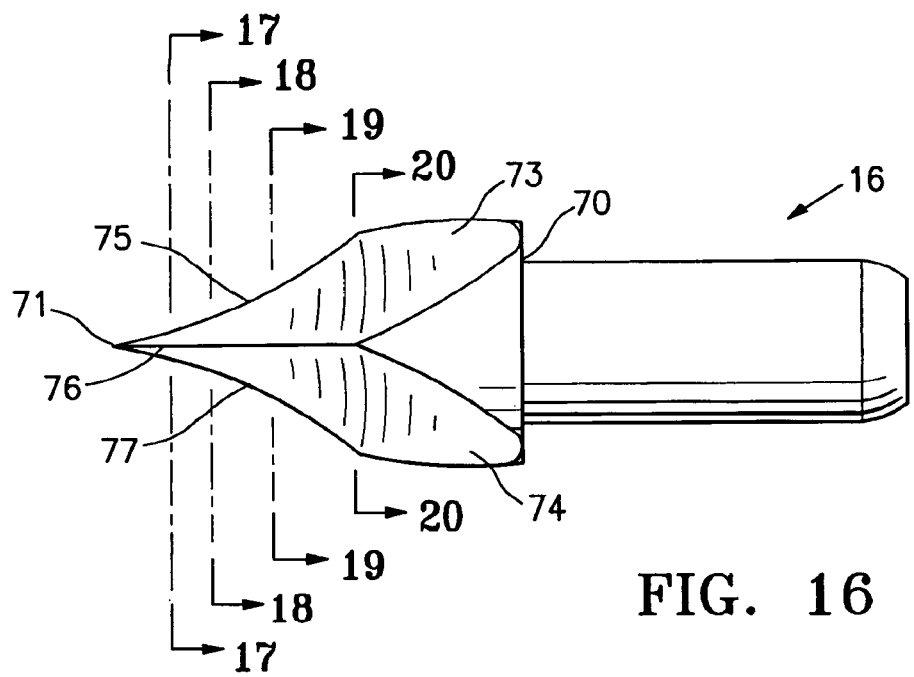
FIG. 16 is a bottom view of the penetrating tip shown in FIG. 10.
Figure 17:
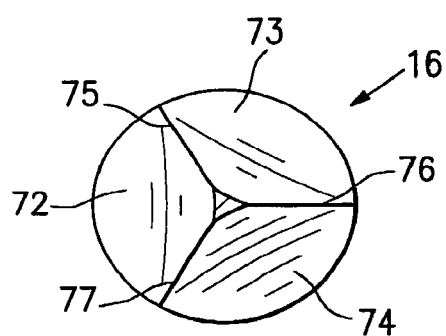
FIG. 17 is a transverse cross-sectional view of the penetrating tip shown in FIG. 16 taken along the lines 17-17.
Figure 18:
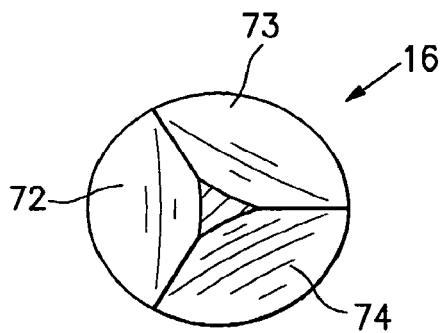
FIG. 18 is a transverse cross-sectional view of the penetrating tip shown in FIG. 16 taken along the lines 18-18.
Figure 19:
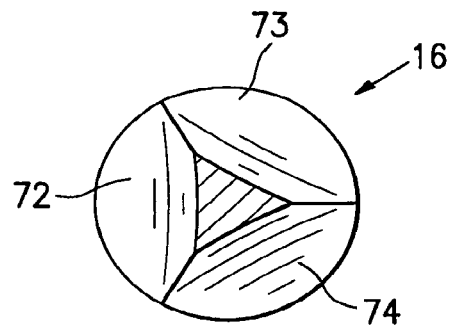
FIG. 19 is a transverse cross-sectional view of the penetrating tip shown in FIG. 16 taken along the lines 19-19.
Figure 20:
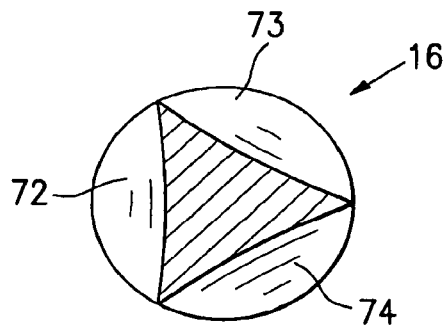
FIG. 20 is a transverse cross-sectional view of the penetrating tip shown in FIG. 16 taken along the lines 20-20.
Figure 21:
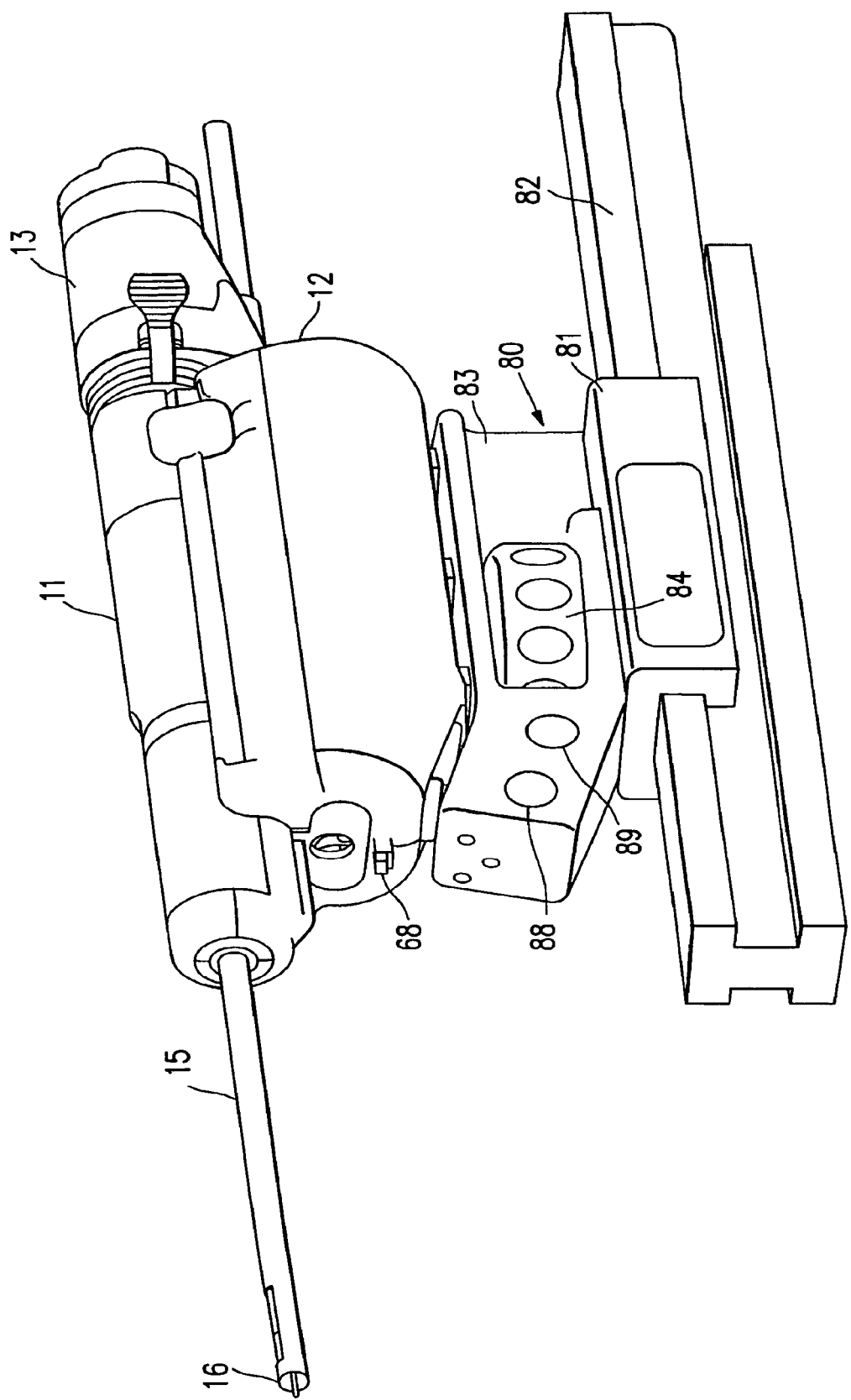
FIG. 21 is a perspective view of the tissue biopsy system shown in FIG. 1 assembled and mounted on a stereotactic frame.
Figure 22:
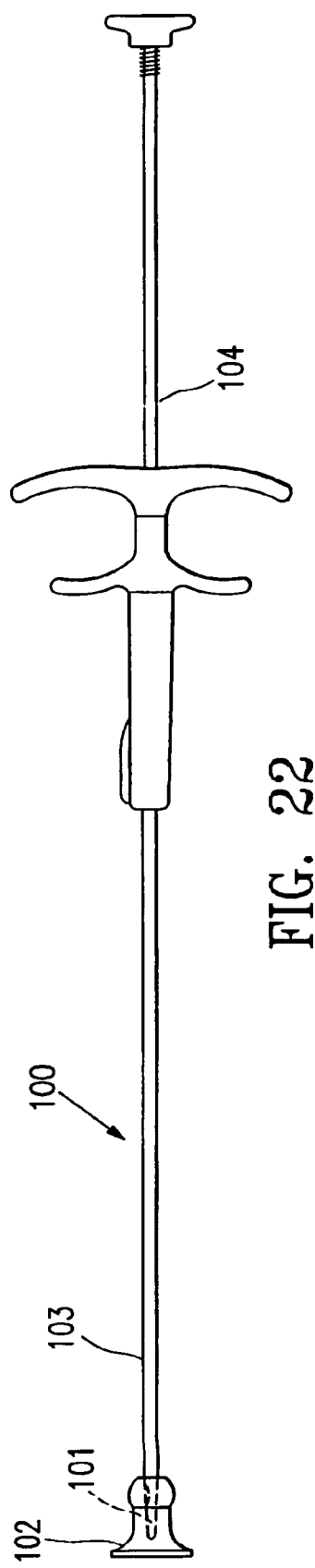
FIG. 22 is an elevational view of a marker delivery device with a flared guide on the distal end of the shaft which facilitates guiding the distal tip of a marker delivery device into the interior of the proximal end of the tissue cutter.

The biopsy system 10 may be hand held for some biopsy procedures or the system may be mounted on a stereotactic mounting stage 80 as shown in FIG. 21. A shoe 81 is slidably mounted to a rail 82 of a Fisher stage. The mounting member 83 is secured to the shoe 81 by a threaded post (not shown) secured to thumbwheel 84. As shown in FIG. 10, the bottom surface 85 of the driver component 12 is configured to conform at least in part to the upper surface of the mounting member 83. The sampling and vacuum switches 86 and 87 respectively on the driver component 12 are actuated by the optional sampling and vacuum actuating elements 88 and 89 on the mounting member 83. Alternatively, sampling and vacuum may be actuated with a foot pedal. As shown in FIG. 22, the driver component has an operator dial 90 which when turned opens a threaded hole 91 for receiving a threaded post (not shown) secured to the thumbwheel 84 and the locating pin holes 92 and 93 which receive the complementary posts (not shown) in the mounting member 83.

As mentioned above, positive pressure or even ambient conditions will aid in passing the severed tissue specimen through the inner lumen 45 of tissue cutter 20 into the cartridge 58 of specimen collector 13. As shown in FIGS. 4A and 4B venting valve can provide ambient pressure behind the tissue specimen in the cutter interior 45 from the interior of the tubular section 15. The valve body 50 is opened for atmospheric venting when the tissue cutter 20 is in the forward position upon the completion of severing the specimen from the tissue site. However, when the tissue cutter 20 is pulled back proximally the valve spring 49 urges the valve body 50 back to a closed position. While the tissue cutter 20 is shown with a tissue cutting surface 21 which is perpendicular to the longitudinal axis 28, the tissue cutting surface may be at an angle or even parallel to the longitudinal axis as described in co-pending application Ser. No. 10/642,406, filed Aug. 15, 2003.

The distal cutting edge 21 of the tissue cutter 20 may initially be located proximal to the aperture 17 to provide a full aperture for receiving tissue or it can be initially located within the aperture 17 in order to control the length of the specimen. The cutting action of tissue cutter 20 preferably continues until the beveled cutting surface 21 has completely traversed the aperture 17 to ensure that the tissue drawn through the aperture is completely severed from supporting tissue at the biopsy site. A vacuum may be applied to aspirate the severed tissue specimen through the inner lumen of the tissue cutter 20 to the cartridge in the specimen collector at the proximal end of the biopsy device. Positive pressure or access to ambient conditions may be provided in the distal end of the tubular section to aid in the specimen transfer.

After the removable wall 57 of the specimen receiving cartridge 58 is removed and the specimens therein removed, it is frequently desirable to deliver one or more markers to the target site from which the specimens have been removed. Such marker delivery devices are shown in co-pending application Ser. No. 10/753,694, filed on Jan. 7, 2004 and co-pending application Ser. No. 10/444,770, filed May 23, 2003. However, the distal ends of these marker delivery devices are very small and they can be difficult to insert into the proximal end of the tissue cutter 20 which is just slightly larger to accommodate the marker delivery shaft.

Figure 23:
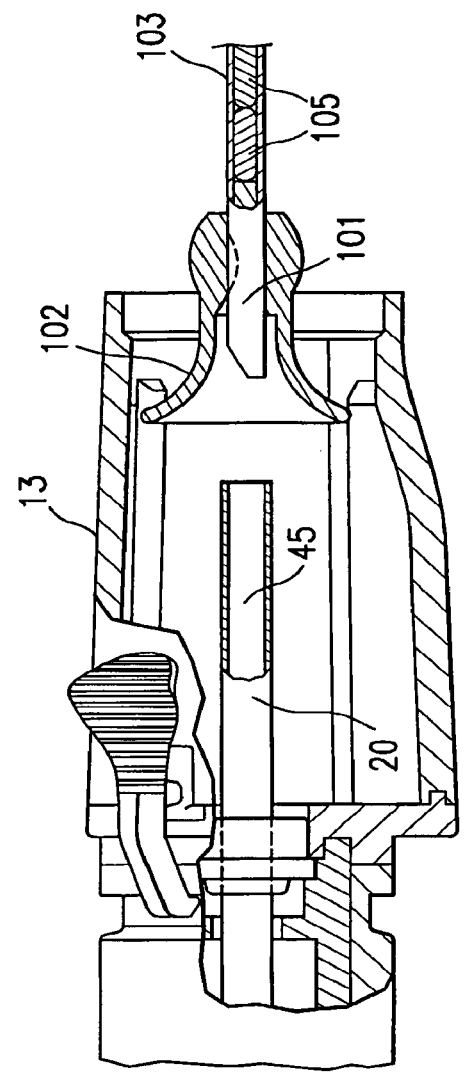
FIG. 23 is a longitudinal cross-sectional view of the distal end of the marker delivery device and flared guide disposed within the tissue collection component shown in FIG. 1.
Figure 24:
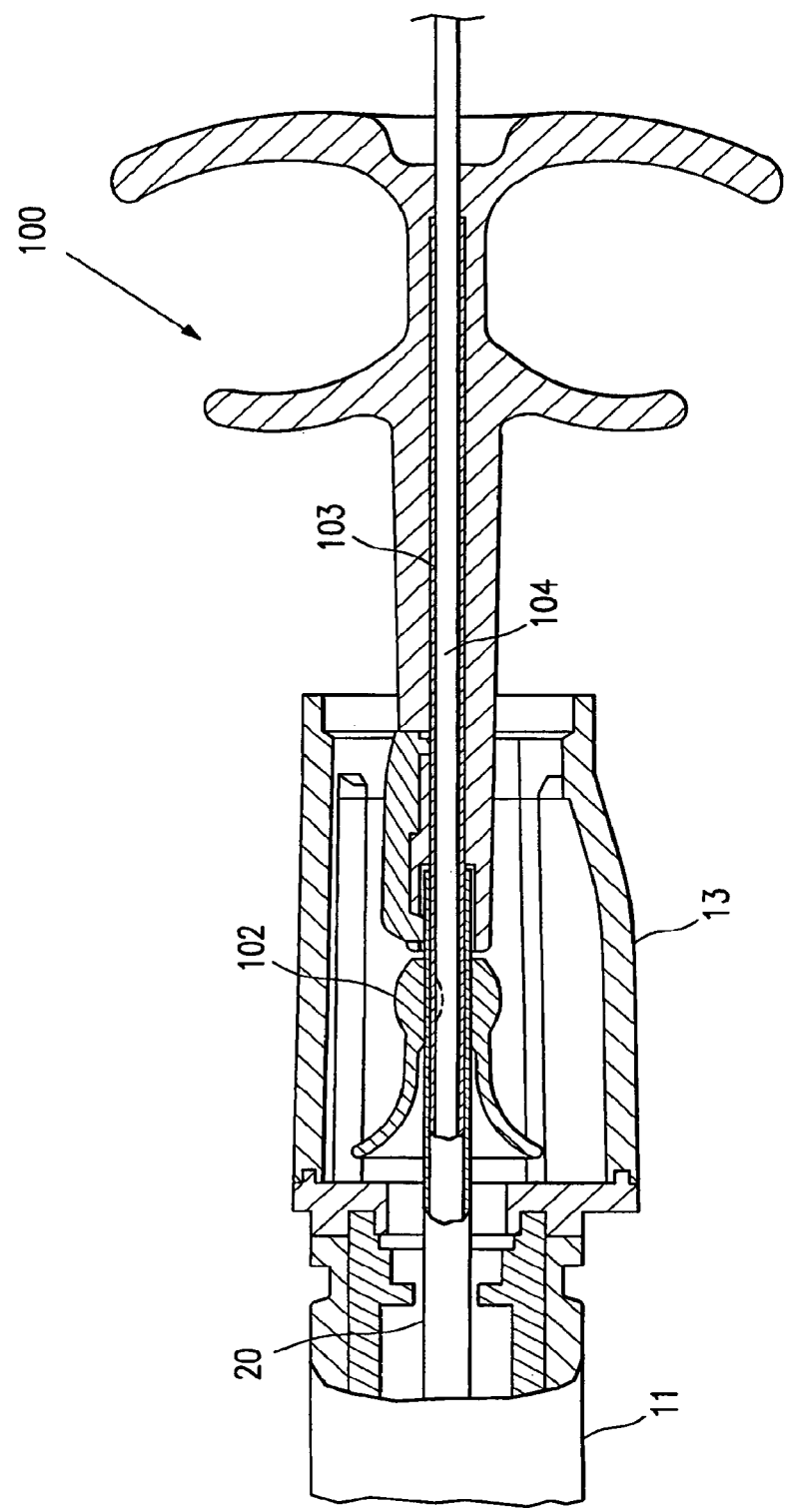
FIG. 24 is a longitudinal cross sectional view of the proximal end of the marker delivery device with the flared guide at the proximal end of the shaft and with the shaft deployed within the inner lumen of the tissue cutter.

FIG. 22 illustrates a marker delivery device 100 which is particularly suitable to facilitate the introduction of the distal end of the shaft 101 into the inner lumen 45 of the tissue cutter 20 and the advancement therein. As shown in FIG. 23, to facilitate the insertion of the small diameter distal tip 101 of the marker delivery device 100 into the slightly larger inner lumen 45 of the tubular cutter 20 at its proximal end, the distal tip is preferably provided with an outwardly flared guide 102 which is slidably mounted on the shaft 103 of the marker delivery device 100. The proximal end of the tubular cutter 20, the flared guide 102 and/or the distal tip 101 may be provided with mating guide elements which orient the marker delivery device with the cannula 15 of the biopsy device. To ensure that one or more markers are discharged through the aperture 17 of the biopsy device 10 when the pusher element slidably disposed within the delivery device is urged distally to press at least one marker body out the discharge opening in the distal portion of the elongated shaft of the marker delivery device. As indicated in FIG. 23, the shaft 103 of the marker delivery device 100 is advanced into the inner lumen 45 of the tissue cutter 20 so that the distal end 101 of the marker delivery device 100 is adjacent to the aperture 17 of the cannula 15. Plunger 104 is pressed further into the inner lumen of shaft 103 to eject one or more markers 105 through the aperture 17 in the tubular section 15 before the biopsy device 10 is removed from the patient. The delivery of markers to the target site after specimen removal, while the distal end of the biopsy device is still at the biopsy site, ensures that the markers are properly position at the biopsy site.

While the slidably mounted, flared proximal guide 102 is described with respect to being disposed on the shaft 103 of marker delivery device 101, the flared guide 102 has wide application within a variety of biopsy and other devices where one small diameter tubular member is to be inserted into a slightly larger, but still small diameter second tubular member.

The elongated probe component 11 of the biopsy system 10 has a length of about 3 to about 20 cm, preferably, about 5 to about 13 cm, and more specifically, about 8 to about 9 cm for breast biopsy use. To assist in properly locating the probe 11 during advancement thereof into a patient's body, the distal extremity of the tubular section may be provided with a marker at a desirable location that provide enhanced visualization by eye, by ultrasound, by X-ray, MRI or other imaging or visualization means. Manual palpation may also be employed. An echogenic polymer coating that increases contrast resolution in ultrasound imaging devices (such as ECHOCOAT™ by STS Biopolymers, of Henrietta, N.Y.) is suitable for ultrasonic visualization. Radiopaque markers may be made with, for example, stainless steel, platinum, gold, iridium, tantalum, tungsten, silver, rhodium, nickel, bismuth, other radiopaque metals, alloys and oxides of these metals. In addition, the surfaces of the device in contact with tissue or other components of the device may be provided with a suitable lubricious coating such as a hydrophilic material or a fluoropolymer.

The tubular section and the tissue cutter are preferably formed of a surgical grade stainless steel. However, other high strength materials such as MP35N, other cobalt-chromium alloys, NiTi alloys, ceramics, glasses, and high strength polymeric materials or combinations thereof may be suitable.

A patient's skin usually must be breached in order to gain access to a body site where a tissue specimen is to be obtained. A scalpel or other surgical instrument may be used to make an initial incision in the skin. After the specimens have been taken, the biopsy device may be removed from the patient. The entire device may be removed; however, in some embodiments, the cartridge 58 may be removed from the system 10 and a delivery cannula may be inserted through the inner lumen of the cutter 20 to deliver markers to the biopsy site through the aperture 17. In addition, it will be readily appreciated that other types of instruments may be inserted into the tissue site through the tissue cutter in addition to or in place of the instruments described above. Moreover, therapeutic or diagnostic agents may be delivered through the tissue cutter 20 or the tubular section 15.

While particular forms of the invention have been illustrated and described herein, it will be apparent that various modifications and improvements can be made to the invention. For example, while the various embodiments of the invention have been described herein in terms of a biopsy device, it should be apparent that the devices and methods of utilizing the device may be employed to remove tissue for purposes other than for biopsy, i.e. for treatment or other diagnoses. Additionally, the tissue penetrating distal tip design may be employed on probes for other uses. Other modifications include, for example, a tissue cutter slidably mounted around the tubular section of the probe component rather than within the tubular section. Moreover, individual features of embodiments of the invention may be shown in some drawings and not in others, but those skilled in the art will recognize that individual features of one embodiment of the invention can be combined with any or all the features of another embodiment. Accordingly, it is not intended that the invention be limited to the specific embodiments illustrated.

Terms such a "element", "member", "device", "section", "portion", "means", "step" and words of similar import, when used in the following claims, shall not be construed as invoking the provisions of 35 U.S.C. § 112(6) unless the claims expressly use the term "means" followed by a particular function without specific structure or the term "step" or "steps" followed by a particular function without specific action. All patents and patent applications referred herein are incorporated by reference in their entirety.

What is claimed is:

1. A biopsy device, comprising:
   an elongated probe having a central longitudinal axis, a proximal end, and a distal end; and
   a tissue penetrating tip that includes a proximal base and a sharp distal point, the proximal base being secured to the distal end of the elongated probe, the sharp distal point being distal to the proximal base and aligned with the central longitudinal axis,
   the tissue penetrating tip having a plurality of concave surfaces annularly arranged to form at least three adjacent pairs of concave surfaces,
   wherein each concave surface of the plurality of concave surfaces extends from the proximal base to the sharp distal point, wherein each adjacent pair of concave surfaces intersect to form a concave curved cutting edge, and cumulatively, the at least three adjacent pairs of concave surfaces form a plurality of concave curved cutting edges that distally terminate at the sharp distal point.

2. The biopsy device of claim 1, further comprising a cutting cannula that is coaxial with the elongated probe.

3. The biopsy device of claim 1, wherein the at least three adjacent pairs of concave surfaces includes a first concave surface, a second concave surface, and a third concave surface that are equi-spaced about the central longitudinal axis of the elongated probe.

4. The biopsy device of claim 3, wherein each of the first concave surface, the second concave surface, and the third concave surface has the same surface area.

5. The biopsy device of claim 3, wherein each of the first concave surface, the second concave surface, and the third concave surface has the same concavity.

6. The biopsy device of claim 1, wherein the plurality of concave curved cutting edges includes a first concave curved cutting edge, a second concave curved cutting edge, and a third concave curved cutting edge,
   each of the first concave curved cutting edge, the second concave curved cutting edge, and the third concave curved cutting edge having the same length in a direction along the central longitudinal axis.

7. The biopsy device of claim 6, wherein the first concave curved cutting edge, the second concave curved cutting edge, and the third concave curved cutting edge are positioned at equal angular intervals around the central longitudinal axis.

8. A tissue penetrating tip for use in a medical device, comprising:
   a proximal base having a central longitudinal axis;
   a sharp distal point located distal to the proximal base, the sharp distal point located on the central longitudinal axis; and
   a plurality of concave surfaces annularly arranged to form at least three adjacent pairs of concave surfaces,
   wherein each concave surface of the plurality of concave surfaces extends from the proximal base to the sharp distal point, wherein each adjacent pair of concave surfaces intersect to form a concave curved cutting edge, and cumulatively, the at least three adjacent pairs of concave surfaces form a plurality of concave curved cutting edges that distally terminate at the sharp distal point.

9. The tissue penetrating tip of claim 8, wherein the at least three adjacent pairs of concave surfaces is three pairs of concave surfaces that define three concave curved cutting edges of equal length that are positioned at equal angular intervals around the central longitudinal axis.

10. The tissue penetrating tip of claim 8, wherein the at least three adjacent pairs of concave surfaces includes a first concave surface, a second concave surface, and a third concave surface that are equi-spaced about the central longitudinal axis of the elongated probe.

11. The tissue penetrating tip of claim 10, wherein each of the first concave surface, the second concave surface, and the third concave surface has the same surface area.

12. The tissue penetrating tip of claim 10, wherein each of the first concave surface, the second concave surface, and the third concave surface has the same concavity.

13. The tissue penetrating tip of claim 8, wherein the plurality of concave curved cutting edges includes a first concave curved cutting edge, a second concave curved cutting edge, and a third concave curved cutting edge,
   each of the first concave curved cutting edge, the second concave curved cutting edge, and the third concave curved cutting edge having the same length in a direction along the central longitudinal axis.

14. The tissue penetrating tip of claim 13, wherein the first concave curved cutting edge, the second concave curved cutting edge, and the third concave curved cutting edge are positioned at equal angular intervals around the central longitudinal axis.

* * * * *